United States Patent
Wang et al.

(10) Patent No.: US 7,981,625 B2
(45) Date of Patent: Jul. 19, 2011

(54) PROSTATE CANCER GLYCAN MARKERS AND AUTOANTIBODY SIGNATURES

(75) Inventors: Denong Wang, Palo Alto, CA (US); Leonore A. Herzenberg, Stanford, CA (US); Donna M. Peehl, Mountain View, CA (US); Leonard A. Herzenberg, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 73 days.

(21) Appl. No.: 12/421,964

(22) Filed: Apr. 10, 2009

(65) Prior Publication Data
US 2009/0258792 A1 Oct. 15, 2009

Related U.S. Application Data

(60) Provisional application No. 61/124,249, filed on Apr. 15, 2008.

(51) Int. Cl.
*G01N 33/53* (2006.01)

(52) U.S. Cl. ........................... 435/7.1; 435/7.2; 436/518

(58) Field of Classification Search ........................ None
See application file for complete search history.

(56) References Cited

U.S. PATENT DOCUMENTS

| | | |
|---|---|---|
| 4,725,557 A | 2/1988 | Miyauchi et al. |
| 5,432,260 A | 7/1995 | Stahl |
| 5,766,853 A | 6/1998 | Parma et al. |
| 2003/0228637 A1 | 12/2003 | Wang |
| 2004/0033546 A1 | 2/2004 | Wang |
| 2008/0071148 A1 | 3/2008 | Bosques et al. |

FOREIGN PATENT DOCUMENTS

| | | |
|---|---|---|
| WO | 2002064556 A2 | 8/2002 |
| WO | 2003016464 A2 | 2/2003 |

OTHER PUBLICATIONS

Denong Wang, et al., "Glycan arrays lead to the discovery of autoimmunogenic activity of SARS-CoV," Physiol. Genomics, May 25, 2004, vol. 18, 245-248.

Jean-Frederic Sanchez, et al., "Biochemical and Structural Analysis of Helix pomatia Agglutinin," J. of Biolog. Chemistry, Jul. 21, 2006, vol. 281, No. 29, 20171-20180.

Gregory T. Carroll, et al., "Photons to illuminate the universe of sugar diversity through bioarrays," Glycoconj J, 2008, 25:5-10.

(Continued)

*Primary Examiner* — Jacob Cheu
(74) *Attorney, Agent, or Firm* — David J. Aston; Peters Verny, LLP

(57) ABSTRACT

Disclosed are methods for probing the immunogenic sugar moieties of prostate cancer cells. The methods detect a number of glyco-epitopes that are highly and differentially expressed among prostate cancers of various Gleason grades. The glyco-epitopes exist on the surfaces of prostate cells. The methods also comprise the detection of autoantibodies in prostate cancer subjects. The antibodies bound to a glyco-motif of N-glycans that is normally "cryptic." This target is highly expressed in prostate cancers. Lectins and antibodies that detect these glyco-epitopes that expressed in prostate cancer tissues include *Euonymus europaeus* lectin (EEL); *Psophocarpus Tetragonolobus* Lectin-I (PTL-I); *Griffonia Simplicifolia* Lectin-I-A4 (GSL-I-A4); *Griffonia Simplicifolia* Lectin-I-B4 (GSL-I-B4); *Sambucus nigra* I agglutinin (SNA-I; *Phaseolus vulgaris*-L (PHA-L; *Galanthus nivalis* agglutinin (GNA); *Narcissus pseudonarcissus* agglutinin (NPA); *Artocarpus integrifolia* agglutinin (Jacalin); and mAb TM10 (IgM).

6 Claims, 14 Drawing Sheets

OTHER PUBLICATIONS

Stephen L. Hart, et al., "Cell Binding and Internalization by Filamentous Phage Displaying a Cyclic Arg-Gly-Asp-containing Peptide," Journal of Biological Chemistry, Apr. 29, 1994, vol. 269, No. 17, 12468-12474.

Istvan Botos, et al., "Structures of the Complexes of a Potent Anti-HIV Protein Cyanovirin-N and High Mannose Oligosaccharides," Journal of Biological Chemistry, Sep. 13, 2002, vol. 277, No. 37, 34336-34342.

Thomas E. Newsom-Davis, et al., "Enhanced Immune Recognition of Cryptic Glycan Markers in Human Tumors," Cancer Res, Mar. 1, 2009; vol. 65, No. 5, 2018-2025.

Alvin Y. Liu, et al., "Characterization of Prostate Cell Types by CD Cell Surface Molecules," Am. J. Pathology, Jan. 2002, vol. 160, No. 1, 37-43.

D. M. Peehl, "Primary cell cultures as models of prostate cancer development," Endocrine-Related Cancer, 2005, vol. 12, 19-47.

Julius S. Horoszewicz, et al., "LNCaP Model of Human Prostatic Carcinoma," Cancer Research, Apr. 1983, vol. 43, 1809-1818.

Hiroaki Tateno, et al., "A novel strategy for mammalian cell surface glycome profiling using lectin microarray," Glycobiology, Aug. 10, 2007, vol. 17, No. 10, 1138-1146.

Ola Blixt, et al., "Printed covalent glycan array for ligand profiling of diverse glycan binding proteins," PNAS, Dec. 7, 2004, vol. 101, No. 49, 17033-17038.

Denong Wang, et al., "Carbohydrate microarrays for the recognition of cross-reactive molecular markers of microbes and host cells," Nature Biotechnology, Mar. 2002, Vo. 20, 275-281.

LecChip Brochure, Moritex Corporation, 2008, 6 pp.

Prostate cancer markers

312 →
310 →
308 →
306 →

304 →
302 →

Lectins/antibodies   SNA     PHA-L    GNA /2G12 and TM10
                              SARS-CoV              HIV-1

PROSTATE CANCER GLYCAN MARKERS AND AUTOANTIBODY SIGNATURES

CROSS-REFERENCE TO RELATED APPLICATIONS

This application claims priority from U.S. Provisional Patent Application No. 61/124,249 filed on Apr. 15, 2008, which is hereby incorporated by reference in its entirety.

STATEMENT OF GOVERNMENTAL SUPPORT

This invention was made with U.S. Government support under National Cancer Institute Grant #1U01CA128416-01. The U.S. Government has certain rights in this invention.

REFERENCE TO SEQUENCE LISTING, COMPUTER PROGRAM, OR COMPACT DISK

None

BACKGROUND OF THE INVENTION

1. Field of the Invention

The present invention relates to the fields of glycan biomarkers and serum anti-glycan antibody signatures of prostate disease.

2. Related Art

Presented below is background information on certain aspects of the present invention as they may relate to technical features referred to in the detailed description, but not necessarily described in detail. The discussion below should not be construed as an admission as to the relevance of the information to the claimed invention or the prior art effect of the material described.

Recent studies suggest that the clinical outcome of prostate cancer highly correlates with the presence of aggressive cancer, including the high volume or percentage of Gleason grade 4/5 cancer and the rapid progressive small cancer in a subject. The Gleason grade is a system to categorize the severity of the cancer based exclusively on differentiation, defined as the resemblance of the cancer cells to the architectural structure of normal prostate glands. The system scores cancers from the well-differentiated grade 1 to the poorly differentiated grade 5. While cells of grade 1 carcinoma closely resemble normal prostate, those of higher grades progressively demonstrate loose aggregation, infiltration of glands into neighboring stroma, and nuclear morphological changes. Particularly, grade 4/5 carcinoma presents a distinct loss of recognizable glandular pattern, replaced by mere sheets of cells with irregular cyto-structures. To determine the final Gleason score, the pathologist examines the biopsy specimen, attempts to grade the two most prominent patterns, and sums up the individual scores.

Given the fact that the presence of aggressive prostate cancer is correlated with the morbidity and mortality of the disease, it is crucial to establish assays not only to detect the presence of prostate cancer but also to differentially detect the presence of aggressive prostate cancer. By reviewing a large amount of experimental and clinical data, Stamey and his colleagues concluded that the percentage of grade 4/5 cancer in the primary tumor is the most significant prognostic marker. However, neither serum PSA levels nor biopsies correctly reveal the volume or grade of cancer in the prostate. Measurement of the percentage of grade 4/5 cancer in a subject can only be achieved after radical prostatectomy. The grade denominators in comparative studies have major influences on the resultant list of genes found to be differentially expressed in prostate cancer. Therefore, it is critical in comparative genetic profiling studies that the histopathology of the tissues be rigorously and precisely defined.

Secondly, investigators rarely distinguish between the expression of a proposed cancer marker in TZ (transition zone) cancer versus PZ (peripheral zone) cancer. The clinical behavior of TZ cancer is very different from that of PZ cancer, and the ideal marker will allow differential diagnosis of these cancers of different zones. Furthermore, the Gleason grades of the cancers are often not precisely defined, but are given instead as a score. A score of 7 is imprecise and does not distinguish a cancer containing 5% grade 4 and 95% grade 3 from one with 5% grade 3 and 95% grade 4. As Stamey and colleagues have shown, the risk of recurrence is vastly different between these two types of cancer, both with a "score" of 7[12]. The biochemical PSA cure rate after radical prostatectomy for men with tumors containing 5% grade 4/5 cancer approaches 90%, whereas that for men with 95% grade 4/5 cancer is about 10%. We presume that genetic changes are the basis of the increased aggressiveness associated with increasing percentages of grade 4/5 cancer, and that grade is a critical variable in genetic profiling studies. Because of the problems described above, many of the published prostate "cancer" markers identified from genetic profiling studies would fail to remain as markers if subjected to more rigorous investigation. In any case, information from genetic profiling has yet to result in a serum marker for prostate cancer.

In 2005, it was reported that autoantibodies against peptides derived from prostate cancer tissue might be used as the basis of a screening test for prostate cancer[20]. Investigators from the University of Michigan used a phage-display library derived from prostate cancer tissue to develop a phage protein microarray to analyze serum samples from men with prostate cancer and controls for autoantibodies. From the initial results, a 22-phage-peptide detector was developed that had 88% specificity and 82% sensitivity in discriminating between the group with prostate cancer and the control group. This panel performed better than PSA in discriminating the two groups. The "autoantibody signature" did not discriminate among different clinical or pathological features such as Gleason grade. It is interesting to note that four of the phage clones represented known proteins, whereas the others were generated from untranslated sequences.

The carbohydrate chains, N-glycans, attached to the single glycosylation site on PSA from normal sera or seminal fluid, as compared with those on PSA from a prostate cancer cell line or the cancer tissues of patients, have been the subject of studies by the groups of Robbins, deLlorens and Fukuda[21-23]. The N-glycans of normal PSA are predominantly biantennary whereas those described on PSA from prostate cancer cells are predominantly tri- and tetra-antennary. The malignant glycoform of PSA from prostate cancer tissue was found to be preferentially bound by the sialyl α2-3-galactose-specific plant lectin *Maackia amurensis*[23]. To overcome the ambiguities associated with the overlap of PSA levels in men with BPH versus cancer, as determined using antibodies raised to the whole glycoprotein, Danishefsky and colleagues[24] have undertaken chemical synthesis of di- tri- and tetra-antennary N-glycans with a view to attaching these to the PSA protein, and thus being able to raise specific antibodies to the normal and malignant glycoforms of the glycoprotein.

Carbohydrate chains are prominently displayed at the surface of cells, attached to glycoproteins and glycolipids. All are potential antigens. Work with naturally occurring and hybridoma antibodies has served to single out carbohydrate antigens that distinguish normal from cancer cells 26-29.

Such tumor-associated antigens have been those expressed exclusively on glycoproteins such as the core regions of O-glycans (T, Tn and sialyl-Tn antigens) or exclusively glycolipids (gangliosides) or shared between glycoproteins and glycolipids: the branched and linear type II backbone regions (I and i antigens), and peripheral regions (blood group A, B, H Lewisa (Lea) and Leb antigens; also blood group-related antigens Lex, Ley, sialyl-Lex and sialyl-Lea, in cells that do not normally express them).

Glycoprotein sugar chain determinants that have been shown to be associated with prostate cancer include those that are formed by very short O-glycans, the T antigen[30, 31] also sialyl Tn, and Tn and also globo-H[32]. These have been among targets selected for immunotherapy in clinical trials[24, 33-35] of prostate cancer. Other manifestations of prostate cancer have been incomplete oligosaccharide synthesis leading to the loss of predicted blood group antigens[36] as on glycolipids[37].

Reverse changes, i.e., increased carbohydrate antigenicities, have also been observed in documented prostatic carcinomas[38], with preservation or increased expression of type II backbone sequences, and with further glycosylation and expression of the difucosylated Ley or the monofucosyl, monosialyl compound sialyl-Lex, Globo H, blood group H, and Leb[39] and also of type I backbone based sialyl sialyl-Lea[40]. In another study, up-regulation of the expression of oligosaccharide sialyl-Lex was considered a new prognostic parameter in metastatic prostate cancer[41].

In summary, a current challenge in prostate cancer research is to identify novel biomarkers, especially serum biomarkers that allow detection of the presence of prostate cancer and determine its aggressiveness. Although considerable efforts have been made, there is so far no solid progress in identification of protein-based novel serum biomarkers of prostate cancer. Key aspects of the present carbohydrate based biomarkers, as discussed below, are a) these carbohydrate structures are immunogenic and thereby elicit specific autoantibodies in prostate cancer subjects and b) detection of autoantibodies targeting these carbohydrate structures allows detection of prostate cancers, especially the presence of aggressive Gleason 4/5 cancers, in a subject. A high-throughput platforms of carbohydrate microarrays as described here will greatly facilitate these tests. In addition, the present invention concerns certain lectins which have been found to bind selectively to prostate markers in different conditions.

SPECIFIC PATENTS AND PUBLICATIONS

Wang et al. Nature Biotechnology 21:275-281, 2002, Proteomics, 3, 2167-2175, 2003) and Physiol. Genomics, 18, 245-9, 2004 describe carbohydrate microarrays.

Wang et al. US PGPUB 2003/30228637 and US 2004/0033546 also describe carbohydrate microarrays, and may be used as guidance in preparation of the present microarrays.

A photo-generated glycan array technology is further described in Langmuir 22, 2899-2905, 2006; Proteomics 7, 180-184, 2007; and Glycoconj J DOI 10.1007/s10719-007-9052-1.

BRIEF SUMMARY OF THE INVENTION

The following brief summary is not intended to include all features and aspects of the present invention, nor does it imply that the invention must include all features and aspects discussed in this summary.

In certain aspects, the present invention comprises a number of glyco-epitopes that are differentially expressed as between normal and cancerous prostate cells. This includes glyco-epitopes that are highly and differentially expressed among prostate cancers of various Gleason grades. In certain aspects, the present invention comprises the detection of auto antibodies in prostate cancer subjects that are bound to a glyco-motif of N-glycans that is normally "cryptic," i.e., not exposed in normal tissue. This target is highly expressed in Gleason 4/5 prostate cancers. In certain aspects, the present invention comprises a panel of lectins for detection of glycan markers bearing distinct glyco-epitopes that are differentially expressed in prostatic cancers. These reagents are useful for binding to prostate tissue and characterizing the tissue as normal, cancerous or subject to benign prostate hyperplasia. The lectins include:

1) *Euonymus europaeus* lectin (EEL), preferred for use in early stage prostate disease detection;
2) *Psophocarpus Tetragonolobus* Lectin-I (PTL-I);
3) *Griffonia Simplicifolia* Lectin-I-A4 (GSL-I-A4);
4) *Griffonia Simplicifolia* Lectin-I-B4 (GSL-I-B4);
5) *Sambucus nigra* I agglutinin (SNA-I), recognizing α2-6 linked Neu5Ac residues;
6) *Phaseolus vulgaris*-L (PHA-L), specific for Tri-II and m-II clusters (known glyco-epitopes); and
7) *Galanthus nivalis* agglutinin (GNA), specific for the Man-core structures, preferred for use in late stage detection, e.g., Gleason stage 4/5.

In certain aspects, the present invention comprises methods and devices which utilize mannose core structures to differentially detect auto-antibodies that are present in patients suffering from diseased prostates. In one aspect, the invention comprises a carbohydrate microarray which binds differentially to antibodies from patients with potentially diseased prostate tissue whereby results from the microarray can characterize a patient as potentially having prostatic tissue which is normal, cancerous, or having benign prostate hyperplasia, wherein said microarray comprises at least one mannose core structure which binds to diseased prostate tissue greater than to normal tissue. Prostatic tissue is characterized as normal, BPH or cancerous, and further characterized as to Gleason grade.

The present devices may include a panel, arranged in individual components, i.e., a microarray, further comprising carbohydrate compounds including (a) for binding to EEL, Galα1, 3Gal; (b) for binding to PTL, GalNac-α; (c) for binding to GSL-I-A4 and GSL-I-B4, GalNac/Galα; (d) for binding to SNA-I, α2-6 linked Neu5Ac; (e) for binding to PHA-L, Tri-II and m-II; and further comprising (f) specific mannose core structures as defined herein. These include, for binding to GNA, high mannose-cluster-1; for binding to NPA, high mannose-cluster-2; for binding to monoclonal antibody TM10, high mannose-cluster-3; for binding to Jacalin, T/Tn antigens, Galα1, 3GalNAc/GalNAcα, etc.

The microarray may further comprise carbohydrate compounds selected from at least one of OR (orosomucoid), AGOR (agalacto-orosomucoid), or ASOR (asialo-orosomucoid) as a negative control in which antibodies do not bind to these carbohydrates. In certain aspects, the present microarray may includes both (man9)n and [(man9)4]n. In certain aspects, it may include man3 or man 5.

In certain aspects, the present invention comprises a method for testing for prostate disease in a subject, comprising the steps of (a) obtaining an antibody-containing sample from the subject; and (b) determining the level of antibody in the subject binding specifically to a mannose core structure. In certain aspects of the present invention, the sample is serum. In certain aspects of the present invention, the mannose core structure is attached to a carrier protein for immobilization in the assay format. In certain aspects, the present method may comprise the step of contacting the sample with OR (orosomucoid) or AGOR (agalacto-orosomucoid) or ASOR (asialo-orosomucoid) as a negative control where antibodies from a patient with prostate cancer do not bind to these antigens but do bind to the mannose core structure.

In certain aspects of the present invention, there is provided a method of determining dysplasia in prostatic tissue, including body fluids derived from such tissue ("tissue material"), comprising the steps of (a) contacting the tissue with EEL lectin; and (b) measuring the amount of EEL lectin bound, where a higher degree of binding is associated with dysplasia and Gleason Grade 3/4 cancer. In certain other aspects, the method may further comprise the step of contacting the tissue with lectin PTL-1; and measuring the amount of PTL-1 bound, where a higher degree of binding is associated with cancerous tissue.

BRIEF DESCRIPTION OF THE DRAWINGS

FIG. 3 is a diagram illustrating that glycan structures where outer sugars are removed in certain instances. The four panels are taken together. In each succeeding panel an outer layer of sugar is removed. In the first panel, the sugars are intact. The diagram illustrates that certain cryptic glycotopes are exposed as the outer sugar residues are no longer added to glycans on a cell surface or certain sugar residues are enzymatically removed. In different degrees of de-glycosylation, sialic residues (shown as indented rectangles) are not present; this is illustrated by ASOR (asialo-orosomucoid); in a greater degree of deglycosylation, both sialic acid and Gal residues (shown as triangles) are missing, as in AGOR (asialo-orosomucoid). OR (orosomucoid) is an abundant human serum glycoprotein. In some cases, only the mannose core structure (rectangles) is present. These are the glycotopes (also termed glyco-epitopes) which are referred to as man clusters below in the present detection methods.

FIG. 7 is a diagram of a lectin array (from Moritex Co. Ltd., Tokyo, Japan) as used in the present work, indicating the identities of the lectins at each location of the array.

DETAILED DESCRIPTION OF THE PREFERRED EMBODIMENT

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The term "lectin" means a non-antibody compound which binds to a specific carbohydrate structure, such as a glycosylated biological molecule, or a glycosylated nanostructure. Because of their ability to recognize complex carbohydrates on cell surfaces with high specificity, lectins play important roles in the social life of cells. Examples of invertebrate lectins include the recognition of "sister" cells as part of the aggregation mechanisms in primitive organisms (e.g., slime molds, sponges and corals), the specific binding of polysaccharide-coated pathogenic bacteria in the innate immunity system of invertebrates, and the mediation of symbiosis, for example between coral and their symbiotic algae. See, Sanchez et al., Biochemical and Structural Analysis of Helix pomatia Agglutinin A Hexameric Lectin with a Novel Fold," *Biol. Chem.*, Vol. 281, Issue 29, 20171-20180, Jul. 21, 2006. Numerous lectins are commercially available, and information on the binding specificity of a given lectin can be obtained from the manufacturer.

Figure 4:
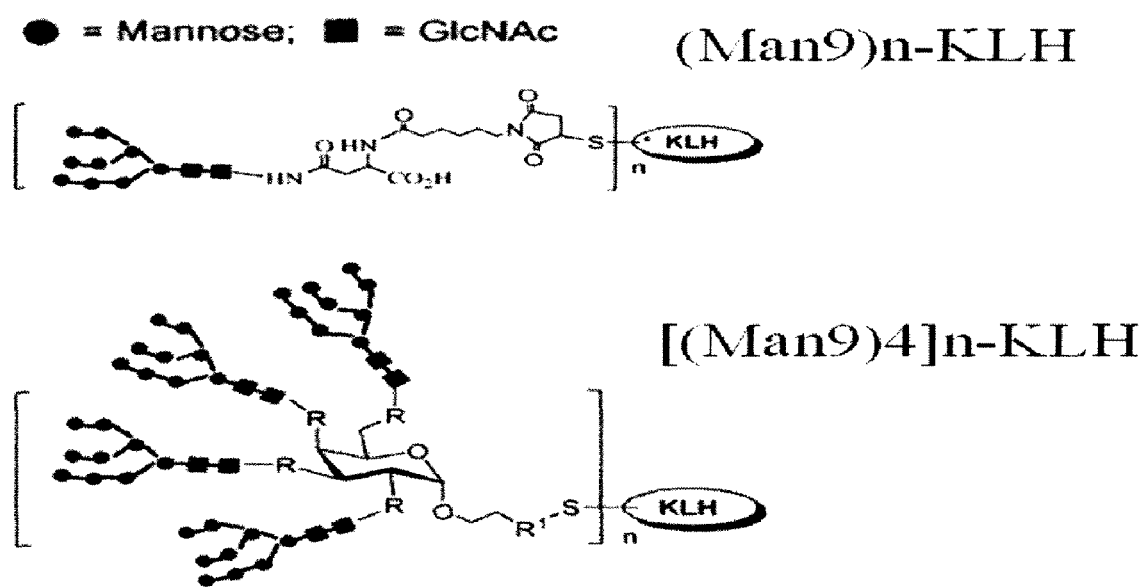
FIG. 4 is a diagram of two different mannose polymers used in the present work to determine autoantibody signatures.

The term "glyco-epitope" means a portion of a polysaccharide chain which has one or more antibody binding epitopes representing an immunological signature by virtue of the polysaccharide composition and/or linkage of monosaccharide subunits. The polysaccharide may have three or more sugar residues. By way of example, a glyco-epitope may be defined by a structure of multiple mannose units, as illustrated in FIG. 3 and FIG. 4. Glyco-epitopes include oligosaccharides in pure or impure or mixed form, and may include such monosaccharides as Man, Gal, Fuc, GalNAc, Sialyl, Fuc1, Hex, Nac5, etc. An exemplary listing of glycan structures which may form different glyco-epitopes is given in Bosques et al., "Glycomic Patterns for the Detection of Disease," US 2008/0071148, published Mar. 20, 2008.

The term "mannose core structure" means a polysaccharide having a branched structure and terminating in a number of mannose sugar units. These structures are found, for example, on glycoproteins as N-glycans. Two examples of mannose core structures are shown in FIG. 4. In (Man9)n-KLH and [(Man9)4]n-KLH, n=multiple repeats of a unit, indicating that a number (e.g., 10s-100s) of units are attached to a single KLH carrier. R is a linking group. R may be benzoyl ether as described in U.S. Pat. No. 5,432,260, or a modified sugar or amino acid. R may also be maleimide and lower alkyl linked through a thiol to a carrier as illustrated for (man9)n-KLH, or other linkage group for attaching the mannose core structure to a support. The KLH carrier supports presentation of Man9 as clusters but other carriers may be used. For example, a BSA carrier may be used, too There are 9 units of mannose comprised in three branches. As can be seen in the figure, the mannose core structure has a GlcNAc attached to a branching chain of mannose units, in this case, three branches of 2-3 mannose units each, 9 total. The (Man9)4 has 4 man 9s on a single sugar. For further details on Man9 and related structures, see Fujiyama et al., "Effect of α1, 2-Mannosidic Linkage Located in α1, 3-Branch of Man6GlcNAc2 Oligosaccharide on Enzyme Activity of Recombinant Human Man9-Mannosidase Produced in *Escherichia coli,*" *J. BIOSCI. BIOENG.*, Vol. 91, 419-421 (2001). In certain embodiments the present mannose core structure is man5; in certain embodiments the present mannose core structure is man9; in certain embodiments the present mannose core structure is man3.

The term "N-glycan" refers to an N-linked oligosaccharide, e.g., one that is attached by an asparagine-N-acetylglucosamine linkage to an asparagine residue of a polypeptide. N-glycans typically have a common pentasaccharide core of $Man_3GlcNAc_2$ ("Man" refers to mannose; "Glc" refers to glucose; and "NAc" refers to N-acetyl; GlcNAc refers to N-acetylglucosamine). The term "trimannose core" used with respect to the N-glycan also refers to the structure Man3GlcNAc.sub.2 ("Man3"). The term "pentamannose core" or "Mannose-5 core" or "Man5" used with respect to the N-glycan refers to the structure Man5GlcNAc2. N-glycans differ with respect to the number of branches (antennae) comprising peripheral sugars (e.g., GlcNAc, fucose, and sialic acid) that are attached to the Man3 core structure.

The term "polysaccharide," as known in the art, refers to a polymeric sugar, also known as a glycan. It is a molecule consisting of a number of monosaccharide (glycose) residues joined to each other by glycosidic linkages. The term here includes in certain instances, or may be limited in certain instances, to oligosaccharides, which are polysaccharides of 2-10 residues. For further details on this definition, see *J. Biol. Chem.*, 257:3352-3354 (1982).

General Description of Materials and Methods

The present description comprises the identification of novel glycan markers of prostate cancers and serum antibody signatures of prostatic cancers. In one example, lectin microarrays were used to explore the glycan-profiles and glyco-epitope profiles of cells from patients with prostate cancers. Further details on the general use and making of a lectin microarrays may be found in Wang, D., Shaoyi L., Trummer, B. J., Deng, C. and Wang, A. Carbohydrate microarrays for the recognition of cross-reactive molecular markers of microbes and host cells (2002), *Nature Biotechnology*, 21, 275-281. In another example, carbohydrate microarrays (glycan arrays) were applied to detect anti-glycan autoantibody signatures of prostate cancers. In another example, prostate cancer tissue microarrays were applied to examine whether the glycan markers identified by the above two methods are indeed present in prostate cancers and tissue expression profiles of these markers.

Thus there is described the identification of novel serum biomarkers of prostate cancers with emphasis on the targets that are valuable for monitoring the malignant transformation and aggressive progression of prostate cancers. Further described is a number of carbohydrate-based biomarkers that are associated with prostate cancers. These biomarkers are the precursors, cores and internal sequences of N-glycans, including high-mannose chains, triantennary type II (Galβ1→4GlcNAc) chains (Tri-II) or multivalent type II chains (m-II). A common characteristic of these markers is that they are masked by other sugar moieties, and they belong to a class of glyco-epitopes that are normally "cryptic". Importantly, their tissue expression or amounts of exposure appear to differ dramatically among different Gleason grades of prostate cancers.

These findings suggest that aberrantly expressed carbohydrates in prostate cancers are immunogenic and are able to induce specific autoantibodies in prostate cancer subjects. Detection of these antibodies in serum allows detection of prostate cancer and monitoring of aggressive progression of the cancer.

Using carbohydrate microarrays, a panel of sera from men with prostate cancer was compared to sera from men with benign prostatic hyperplasia (BPH) who are biopsy-negative for cancer. In the cancer sera, it was found that one may detect significant amounts of autoantibodies specific for some glyco-epitopes that are highly expressed in prostate cancers. These findings are summarized in the subsequent sections.

Carbohydrate microarray technologies, especially different platforms of carbohydrate arrays, are provided as a powerful means to facilitate the exploration of the immunogenic sugar moieties and the repertoires of autoantibodies targeting these moieties. The microarray platform has a number of technical advantages. First, its large capacity: a diverse panel of antigens and antibodies can be displayed in a limited amount of chip space. Second, the high detection sensitivity: each preparation is spotted in an amount that is much smaller than that required for a conventional molecular or immunological assay. In such a miniaturized assay system, the antigen-antibody interaction takes place under the "ambient analyte condition"42, 43 that allows binding to occur rapidly, resulting in highly sensitive detection results.

The structure of a given carbohydrate described here is further explained in Aoki-Kinoshita, "An Introduction to Bioinformatics for Glycomics Research," *PLoS Comput Biol*

4(5): e1000075 2008 and (WO/2003/016464) Cancer Specific Oligosaccharide Sequences and Uses Thereof, published 27 Mar. 2003.

Given the specificities of the lectins described here, it is understood that the lectins may be used to detect the presence, absence, or amount of a prostate cell surface marker in cell assay, semen, urine, serum, or other materials into which the cell surface sugars, which are recognized by these lectins, are shed. In addition, the lectins may be modified for ease of manufacture and consistent quality. For example, a lectin (e.g., EEL) may be used to identify a specific carbohydrate binding partner, which then in turn may be used to generate an antibody which has the same binding specificity as the EEL lectin does to the prostate marker.

EEL, *Euonymus Europaeus* Lectin, is a glycoprotein of about 140,000 daltons, which consists of six closely related lectins with isoelectric points between pH 4.3 to pH 4.7. Most of the 35,000 Dalton subunits appear to consist of two disulfide linked chains of about 17,000 Daltons. This lectin has a carbohydrate binding specificity toward type 1 or type 2 chain blood group B structures but will bind other oligosaccharides containing galactosyl (α-1,3) galactose. Unlike *Ulex europaeus* and *Lotus tetragonolobus* lectins, EEL has a high affinity toward type 1 chain blood group H structures.

Specificity of a given lectin may be confirmed by competition experiments comparing binding of the lectin and a known antibody. Carbohydrate mimicking peptides are described in "Preparation of peptides, which mimic glycosphingolipids by using phage peptide library and their modulation on β-galactosidase activity," *FEBS Letters*, Volume 418, Issue 1-2, Pages 219-223, T. Taki.

Peptides that bind to the MBL (mannose binding lectin) may also be identified by conventional screening methods such as phage display procedures (e.g., methods described in Hart, et al., *J. Biol. Chem.* 269:12468 (1994)). Hart et al. report a filamentous phage display library for identifying novel peptide ligands for mammalian cell receptors. In general, phage display libraries using, e.g., M13 or fd phage, are prepared using conventional procedures such as those described in the foregoing reference. The libraries display inserts containing from 4 to 80 amino acid residues. The inserts optionally represent a completely degenerate or a biased array of peptides. Ligands that bind selectively to MBL are obtained by selecting those phages, which express on their surface a ligand that binds to the MBL. These phages then are subjected to several cycles of reselection to identify the peptide ligand-expressing phages that have the most useful binding characteristics. Typically, phages that exhibit the best binding characteristics (e.g., highest affinity) are further characterized by nucleic acid analysis to identify the particular amino acid sequences of the peptides expressed on the phage surface and the optimum length of the expressed peptide to achieve optimum binding to the MBL. Alternatively, such peptide ligands can be selected from combinatorial libraries of peptides containing one or more amino acids. Such libraries can further be synthesized which contain non-peptide synthetic moieties which are less subject to enzymatic degradation compared to their naturally-occurring counterparts. Peptides and antibodies which bind to the glycans described here may similarly be developed and used as part of a carbohydrate array used to detect auto antibodies.

To determine whether an antibody, antibody fragment, affibody or like peptide or polypeptide binds to a subject lectin, any known binding assay may be employed. For example, the lectin may be immobilized on a surface and then contacted with a labeled antibody. The amount of lectin that interacts with the peptide or the amount which does not bind to the peptide may then be quantitated to determine whether the peptide binds to the lectin. A surface having the deposited monoclonal antibody immobilized thereto may serve as a positive control.

Screening of peptides also can be carried out utilizing a competition assay. If the peptide being tested competes with the deposited monoclonal antibody, as shown by a decrease in binding of the deposited monoclonal antibody, then it is likely that the peptide and the deposited monoclonal antibody bind to the same, or a closely related, epitope. Still another way to determine whether a peptide has the specificity of the deposited monoclonal antibody of the invention is to pre-incubate the deposited monoclonal antibody with the lectin with which it is normally reactive, and then add the peptide being tested to determine if the peptide being tested is inhibited in its ability to bind the lectin. If the peptide being tested is inhibited then, in all likelihood, it has the same, or a functionally equivalent, epitope and specificity as the deposited monoclonal antibody.

One may also obtain antibodies to the lectin or a prostatic tissue biomarker. By using these antibodies, it is possible to produce anti-idiotypic antibodies which can be used to screen other antibodies to identify whether the antibody has the same binding specificity as the anti-lectin monoclonal antibodies. In addition, such anti-idiotypic antibodies can be used for active immunization (Herlyn, et al., Science, 232:100, 1986). Such anti-idiotypic antibodies can be produced using well-known hybridoma techniques (Kohler and Milstein, Nature, 256:495, 1975). An anti-idiotypic antibody is an antibody which recognizes unique determinants present on the monoclonal antibodies. These determinants are located in the hypervariable region of the antibody. It is this region which binds to a given epitope and, thus, is responsible for the specificity of the antibody. An anti-idiotypic antibody can be prepared by immunizing an animal with monoclonal antibodies. The immunized animal will recognize and respond to the idiotypic determinants of the immunizing deposited monoclonal antibodies and produce an antibody to these idiotypic determinants. By using the anti-idiotypic antibodies of the immunized animal, which are specific for the monoclonal antibodies of the invention, it is possible to identify other clones with the same idiotype as the deposited monoclonal antibody used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

Further experimental details for such a method are given in U.S. Pat. No. 4,725,557 to Miyauchi, et al. entitled "Production of fucosyl antigens and antibodies for recognizing same determination of cancer associated carbohydrate linkage using same and kit for the determination." Other binding mimics are also known, such as nucleic acid "aptamers," as described e.g., in U.S. Pat. No. 5,766,853 to Parma, et al., entitled "Method for identification of high affinity nucleic acid ligands to selectins."

Other lectins disclosed here may be engineered in the same way as EEL, since their characteristics are known. Lectin characteristics may be first identified in the LECster database or the Handbook of Plant Lectins. As another example, PTL-I is a basic glycoprotein with a molecular weight of about 58,000. This lectin is a dimer of two closely related subunits, and has an isoelectric point above pH 9.5. Binding occurs with carbohydrate structures containing alpha linked galactosamine. Lactose and other beta-linked galactosides are poor inhibitors of binding. One may therefore use these binding characteristics to obtain molecules having the same binding properties and selectivity, as described above.

An example of a monoclonal antibody which binds to a carbohydrate antigen exposed in prostate disease is murine monoclonal antibody TM10. TM10 is described in Newson-Davis et al., "Enhanced Immune Recognition of Cryptic Glycan Markers in Human Tumors," Cancer Res. 69(5):2022-2025 (Mar. 1, 2009). It was produced from mice vaccinated with fasL-expressing B16F10 mouse melanoma cells and screened in a carbohydrate array of the type described herein. The antigenic target of the monoclonal antibody is a high-mannose core structure. The monoclonal antibody binds strongly to (Man9)n, representing the mannose core of N-glycoproteins and also binds strongly to [Man9)4]n, which mimics the mannose clusters displayed by the gp120 glycoprotein of HIV-1. The term "high mannose cluster" means a branched oligosaccharide having a structure essentially identical, or identical, to these oligosaccharides. TM10 did not bind to any other antigens on the array or to other antigens tested. It recognizes a variety of tumor cells. Thus TM10 may be used to detect the cryptic core structures derived from the surfaces of diseased prostate. It also has a binding specificity which may be expected to be seen in antibodies of patients with diseased prostates.

The criteria for target selection in the preparation of a carbohydrate array are a) the antigen detects prostate cancer-associated autoantibodies in serum; b) antibody detection of the antigen shows significant correlation to either low grade (Gleason 1-3) cancer and/or the progressive, high volume Gleason 4/5 cancers; c) the desired glyco-epitope of the antigen is stable on chips for at least six months; and d) the antigen is inexpensive and has a stable source. The last criterion is optional, but may be important for future application of this assay.

One has the option of using either the nitrocellulose-based bioarray platform or the photo-generated glycan arrays.

As referenced above, the glycoepitopes on the diseased prostate tissue as described here present targets for therapeutic intervention. That is, one may prepare therapeutic or imaging compounds, which comprise the disclosed lectins or polypeptides or nucleic acids having the same binding properties as the lectins disclosed. The lectins will bind only to diseased prostate tissue. In addition, vaccines may be prepared using the cell surface structures disclosed below as being recognized by prostate cancer patients' autoantibodies. These therapeutic vaccines will potentiate the natural defense mechanism exhibited by the autoantibodies characterized here.

Figure 1:
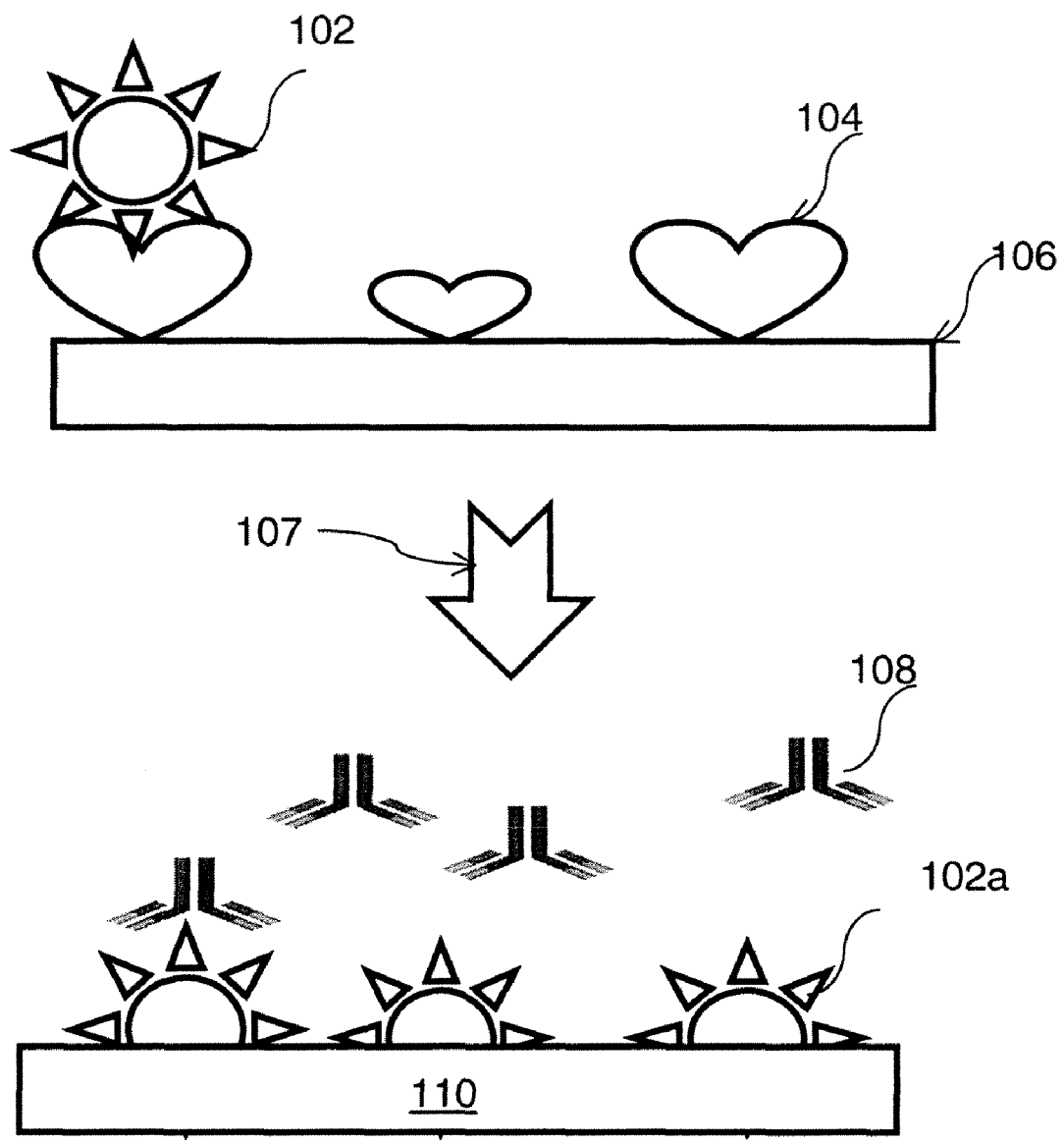
FIG. 1 is a schematic representation of a lectin array having certain lectins according to the present invention that bind to glyco-epitopes which are differentially expressed on abnormal prostatic cells, leading to the use of a carbohydrate array for the detection of autoantibodies differentially present in the sera of cancer patients.

A generalized representation of the various embodiments of the present invention is shown in FIG. 1. There, an array of different lectins is shown at the top of the figure. The lectins are contacted with glycoproteins of prostate cancers and those of normal prostate cells as a control. Lectins 104 are attached to a substrate. Three different lectins, having different glycan binding specificities are illustrated, but in practice more will be used. Any number of different lectins can be used. Exemplified below is an array with approximately 45 different lectins. Each lectin may be spotted in duplicate, triplicate, etc. A glyco-epitope 102 is shown binding to a specific lectin. In practice, the glyco-epitope 102 is present in a mixture of glycoproteins expressed by cells or fluid components obtained from specimens that are either known as being associated with a certain type of prostatic tissue or are being tested for prostate dysplasia. In a second stage, indicated by arrow 107, the glyco-epitopes 102a as previously isolated as being significantly differently expressed in different types of prostate conditions are themselves attached to a substrate and used as probes in an array. The glyco-epitopes 102a need not be identical to the original glyco-epitopes as tested against lectins, but will have the same binding specificity to antibodies 108. As described below, a preferred glycoepitope 102a on the array is in a mannose core structure. Serum antibodies 108 from patients being evaluated are contacted with the glyco-epitopes as contained in the carbohydrate array 110. The glyco-epitopes 102a are, in a preferred embodiment, based on a mannose core protein, essentially as shown and described below. The glyco-epitopes are exposed on cell surfaces in diseased prostate tissue, especially cancerous tissue.

The prostate gland has two generic cell types: epithelial and stromal. Either may be used here. Particular cells, cell types or membrane preparations may be prepared according to a desired target cell type. The cells may be characterized according to CD markers for a specific application of a carbohydrate panel. See, Liu and True, "Characterization of Prostate Cell Types by CD Cell Surface Molecules," *American Journal of Pathology,* 2002; 160:37-43. For example, a comparison of the CD profiles of non-neoplastic cells with profiles of cancer cells gives support to the hypothesis that prostate carcinoma cells arise from luminal rather than basal cells. Most primary tumors contain CD57+ cancer cells; these cells are not stained by the basal cell markers CD44, CD 104, or CD99R. One marked difference between CD57+ cancer cells and CD57+ luminal cells is the absence of CD13 expression in the former. One may also use as the glycoepitope a carbohydrate structure associated with metastatic prostate cancer cells. That is, microvascular endothelium of metastasis-prone tissues is known to undergo activation in response to desialylated cancer-associated carbohydrate structures such as Thomsen-Friedenreich (TF) antigen (Gal{beta}1-3GalNAc) expressed on circulating glycoproteins and neoplastic cells.

Thus the glyco-epitope testing as shown in FIG. 1 (top) may be employ glyco-epitopes derived from cells used whole, or prostate cells that are processed according to standard techniques to obtain a cell membrane preparation. Also, carbohydrates in seminal fluid, such as PSA or other carbohydrate components, may be tested against various lectins. According to the methods described below, one detects differential binding between a prostate tissue glycan-containing component and one or more of the lectins tested (FIG. 1, top). This may present a novel diagnostic method or apparatus, comprising the use of the lectin that is differentially bound by patient prostate tissue samples depending on the prostate status of the patient.

The above methods will also give rise to a further aspect of the present invention. That is, as shown by the arrow 107 in FIG. 1, identification of diagnostic glyco-epitopes enables, according to the teachings set forth here, the isolation and use of the glyco-epitopes identified in this way as probes in a carbohydrate-based test or a test for the presence of anti-carbohydrate antibodies in bodily fluids. The glyco-epitopes may be present on synthetic carbohydrates or in native carbohydrate antigens, including polysaccharides, glycolipids and glycoproteins, etc. It is shown below that prostate malignancy causes a different pattern of cell glycosylation, uncovering cryptic antigens, with the result that a patient may develop auto-antibodies to these carbohydrate antigens. Exemplified below is the use of synthetic high mannose clusters with different cluster configurations. Alternatively, using the guidance provided here, carbohydrates can be prepared directly and tested against sera from prostate patients and normal subjects. The preparation of different platforms of carbohydrate arrays is described in a number of publications, including inventor Wang's group ((Wang, et al., Nature Biotechnology 21:275-281, 2002, Proteomics, 3, 2167-2175, 2003) and Physiol. Genomics, 18, 245-9, 2004)) and by other groups, e.g., Dukler et al., "Complex Carbohydrate Arrays and Methods for the Uses Thereof," WO/2002/064556. In one preferred method, antibodies binding to the carbohydrates are detected by labeled secondary antibodies, such as anti-human IgG or IgM. In a preferred method, photo-generated glycan arrays are prepared from synthetic saccharide libraries which are microspotted onto a photo-reactive surface, such as a glass slide coated with a self assembled monolayer. See, e.g., Michel Olaf, Ravoo Bart Jan Carbohydrate Microarrays by Microcontact "Click" Chemistry. Langmuir: the ACS journal of surfaces and colloids, vol. 24 n. 21 pp: 12116-12118 (2008).

Example 1

Tissue Microarray for a Comparative Analysis of Glyco-Epitope Expression Among Prostate Cancers of Different Gleason Grades Recent establishment of tissue array technology provides a powerful means to further explore the application of immunological probes, i.e., the well-characterized anti-carbohydrate antibodies and lectins, in identification of prostate-cancer-associated/specific carbohydrate moieties. This technology allows simultaneous detection of glycan-expression by an array of tissues spotted on glass-slides. This facilitates comparative measurement of the expression levels of glyco-epitopes among different grades of prostate cancers and control tissues.

Figure 2:
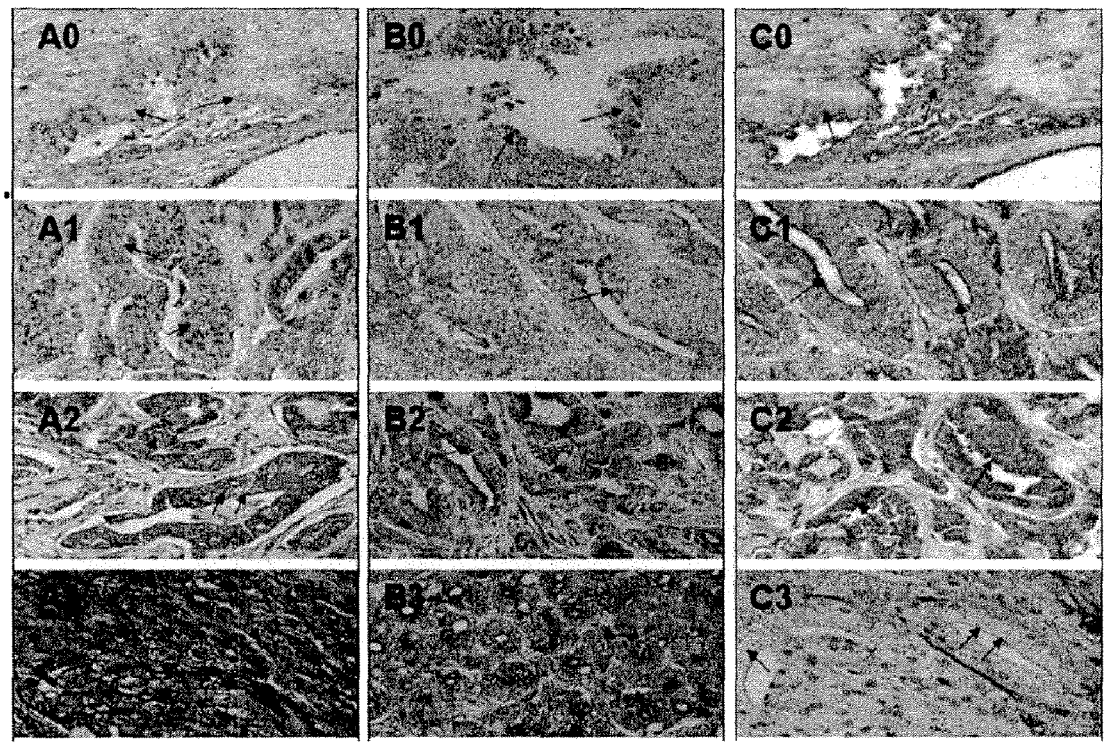
FIG. 2 is a series of 12 photographs showing lectin GNA, PHA-L and SNA (also termed SNA-1) histochemistry of benign prostate hyperplasis (BPH) and adenocarcinoma of various Gleason grades (1-5). Columns A, B, and C are stained by lectins GNA, PHA-L and SNA respectively. Row 0=BPH: Row 1=Prostate adenocarcinoma scored by the Gleason system as grade 1; Row 2=Gleason 2/3, and Row 3=Gleason 4/5. Expression of cryptic glyco-epitopes in prostate cancers is illustrated by staining of the indicated lectins in the indicated malignancy grade.

Three lectins of known specificities were used to detect expression of various N-glycan types among prostate adenocarcinomas of different Gleason grades. These are: 1) *Sambucus nigra* I agglutinin (SNA-I), recognizing α2-6 linked Neu5Ac residues; 2) *Phaseolus vulgaris*-L (PHA-L), specific for Tri-II and m-II clusters and 3) *Galanthus nivalis* agglutinin (GNA), specific for the Man-core structures. Referring now to FIG. 2, there are illustrated lectin GNA, PHA-L and SNA histochemistry of benign prostate hyperplasia (BPH) and adenocarcinomas of various Gleason grades (1-5). BPH and prostate cancer tissue arrays (US Biomax, Inc., Rockville, Md.) were stained by biotinylated lectins and developed with Streptavidin-HRP conjugate and DAB substrate. Lectins were pre-titrated and applied at 10 μg/ml for staining.

In FIG. 2, the tissue photomicrographs are arranged in columns by lectin and rows by degree of malignancy. Columns A, B, and C are stained by lectin GNA, PHA-L and SNA respectively. BPH: A0, B0 and C0; Prostate adenocarcinoma scored by the Gleason system as grade 1, 2/3, and 4/5. That is, in lower rows, the same lectins are stained in cells having increasing stages of malignancy. The results are as follows:
1) GNA stain (Column A): In BPH (A0), the stroma and glandular cells (black arrows) demonstrate only mild and sparse staining. In adenocarcinoma scored by the Gleason system as 1 (A1), the luminal borders of the gland cells (black arrow) show stronger staining than BPH. In Gleason grade 2/3 adenocarcinoma (A2), the entire gland (arrows) demonstrates more intense staining than Gleason 1. In Gleason 4/5 adenocarcinoma (A3), GNA shows the most intense staining.
2) PHA-L stain (Column B): In BPH (B0), PHA-L stains the luminal borders of the gland cells fairly mildly. Similar to the situation in GNA staining, in Gleason 1 adenocarcinoma (B1), PHA-L stains the luminal border of gland cells (black arrows) more intensely. This staining of luminal borders (arrowheads) increases in intensity in Gleason 2/3 adenocarcinoma (B2). In Gleason 4/5 adenocarcinoma (B3), PHA-L shows the strongest staining.
3) SNA stain (Column C): In contrast to GNA and PHA-L, SNA demonstrates strong, intense staining of the luminal gland borders (black arrows) of BPH (C0). The staining of glandular borders (black arrows) remains high for adenocarcinoma of Gleason 1 and 2/3 (C1 and C2). In Gleason 4/5 adenocarcinoma (C3), SNA staining becomes negative (black arrows).

In summary, the above lectin staining of tissue arrays suggests that prostate cancers express a number of complex carbohydrate moieties that are not present or are expressed at lower levels in benign prostate tissues. Given the specificities of these lectins, these targets are likely core-structures or internal sugar chains of N-glycans. These core carbohydrate structures that are differently expressed as malignancy progresses include a) Tri-/m-II, which are highly reactive with PHA-L and are expressed by a human serum glycoprotein asialo-orosomucoid (ASOR) 44, 50, 51; b) Tri-/m-Gn, which are the agalactosyl derivatives of Tri/m-II and are present in the agalactosyl ASOR (AGOR), and c) Man-cores. This is supported by our microarray characterization of the binding specificities of PHA-L and GNA that were used for immunohistology. GNA is highly reactive with Man-cores and Man-clusters and the Tri-/m-Gn structural units (data not shown). PHA-L differs from GNA in that it is highly reactive with Tri/m-II but has no binding to Man-clusters and Tri-/m-Gn. (See FIG. 3, showing cryptic glycotopes, for schematics of the structural relationship of Man-cores, Tri-/m-Gn, and Tri/m-II and glycoprotein, AGOR, ASOR and OR, that express these sugar moieties.

The above was developed as a result of primary culture of epithelial cells from normal and malignant human prostate tissues. Such primary cultures have been widely used as an in vitro experimental model of normal and diseased prostate biology (Peehl, D. M. Primary cell cultures as models of prostate cancer development. Endocrine-related Cancer 12:19-47, 2005.). Lectin arrays were used to conduct a comparative analysis of glycan profiles among cultures from normal prostate, benign prostatic hyperplasia (BPH) and prostate cancers. Interestingly, among a panel of forty-five lectins spotted in the arrays, only EEL was strongly bound by the cell culture lysate derived from a Gleason grade 3/4 prostate cancer. Lysates of BPH and normal cell cultures were negative or weakly bound. This assay was repeated three times and produced the same results.

Immunohistology Validation of Microarray Findings

Using the unique resources of Stanford Prostate Cancer Bank, we stained prostate cancer tissue with a panel of lectins. Results of the lectin immunohistochemistry are briefly summarized below:
i) Normal prostate: EEL stained blood vessels but not prostate epithelial cells, glands and secretions in both samples ii) Dysplasia (PIN): the lectin stained the prostatic epithelial cells and the luminal surfaces of areas of dysplasia; iii) Gleason 3 and 4 cancers: the lectin generally stained strongly the cancer cells that were relatively rich in cytoplasmic contents and stained most strongly the luminal secretions in the Gleason 3 cancer areas, iv) Gleason 5 cancer: there was a complete lack of EEL staining in the cancer tissue except in the capillary blood vessel structures. EEL was also generally negative in the mucin-type Gleason 3 cancers (data not shown).

Figure 14:
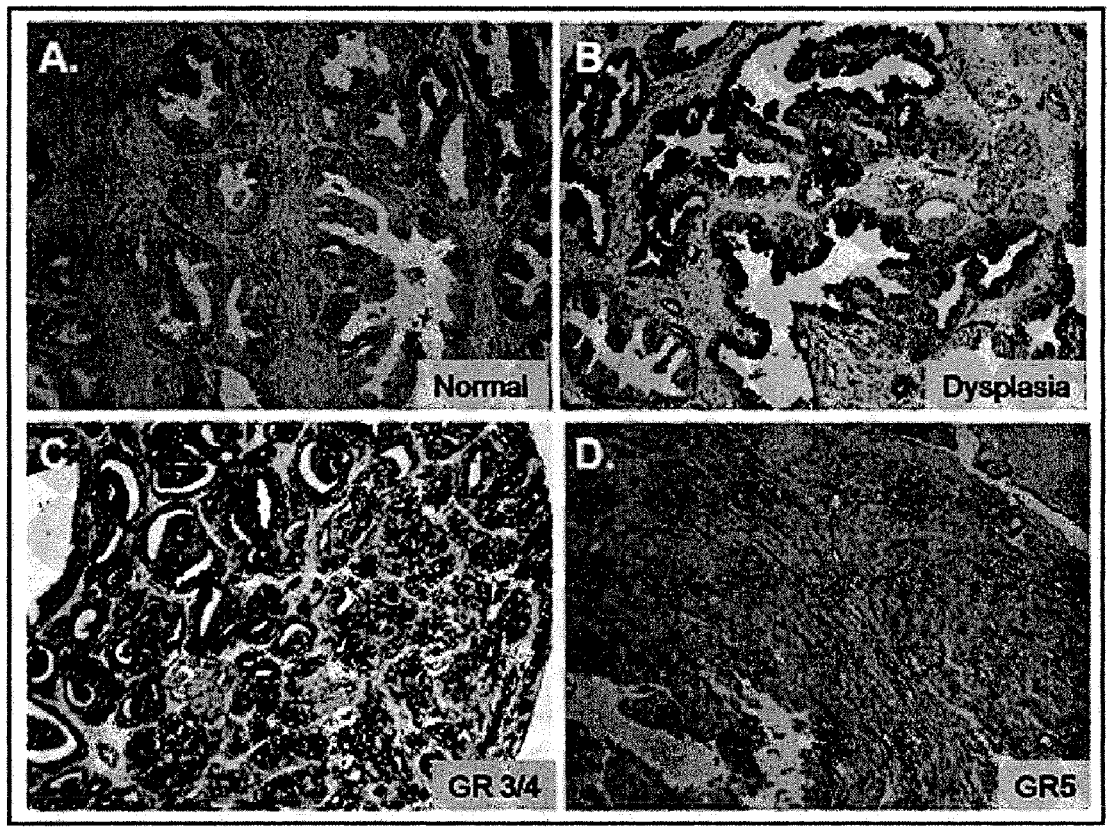
FIG. 14 is a series of four photographs (A-D) illustrating histochemistry of the tissues indicated in each panel stained with biotinylated lectin EEL and developed with streptavidin-HRP conjugate and DAB substrate.

FIG. 14 shows that EEL used in staining tissue, recognized a glycan marker highly expressed in prostatic dysplasia and Gleason grade 3 and 4 cancers but negative in Gleason 5 cancers; in FIG. 14A, normal tissue shows very little staining; in FIG. 14B, dysplasia shows staining around the lumens; GR 3/4 shows diffuse staining throughout; and GR5 (Panel D) shows a different morphology, but little staining.

Collectively, the results show that the EEL-ligands are normally expressed in blood vessels, but are aberrantly expressed in prostate cancer cells and secretions produced in some (but not all) grade 3/4 cancers and in some pre-cancer dysplastic (PIN) structures. EEL-ligands are lacking in the mucin-type G3 cancer and in the Gleason 5 cancer so far analyzed. Potential of these glycan markers and autoantibodies to them in the early detection, differential diagnosis and prognosis of prostate cancer can be exploited by known assay techniques, given the present teachings.

Example 2

Use of Lectin Arrays to Detect Glyco-Epitopes

Figure 7:
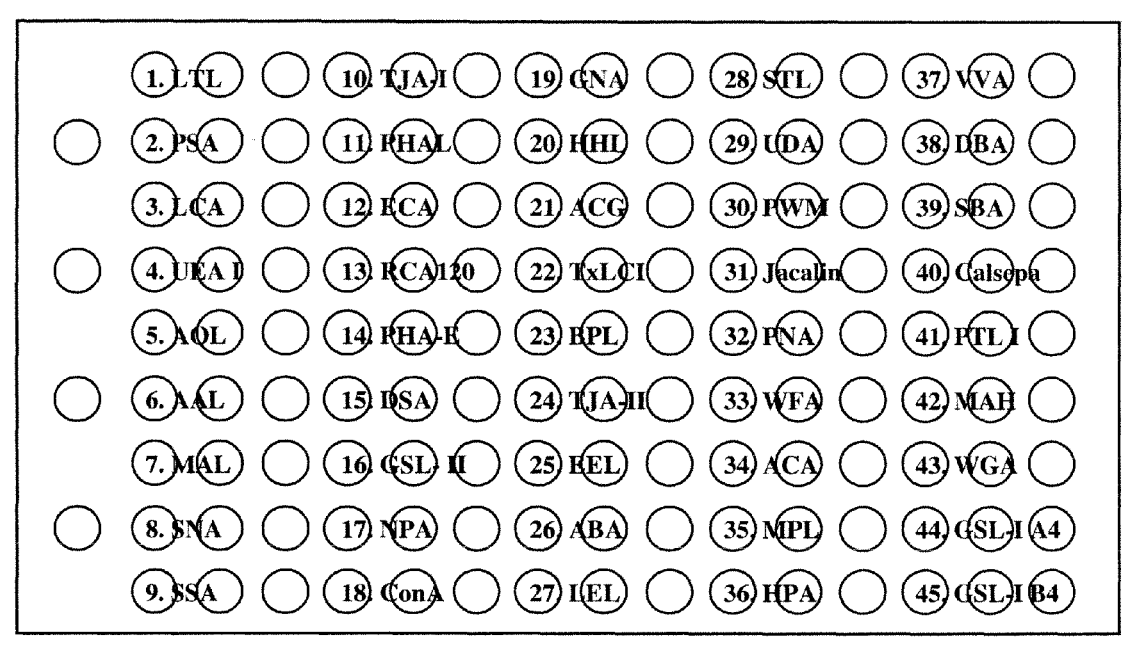
Figure 8:
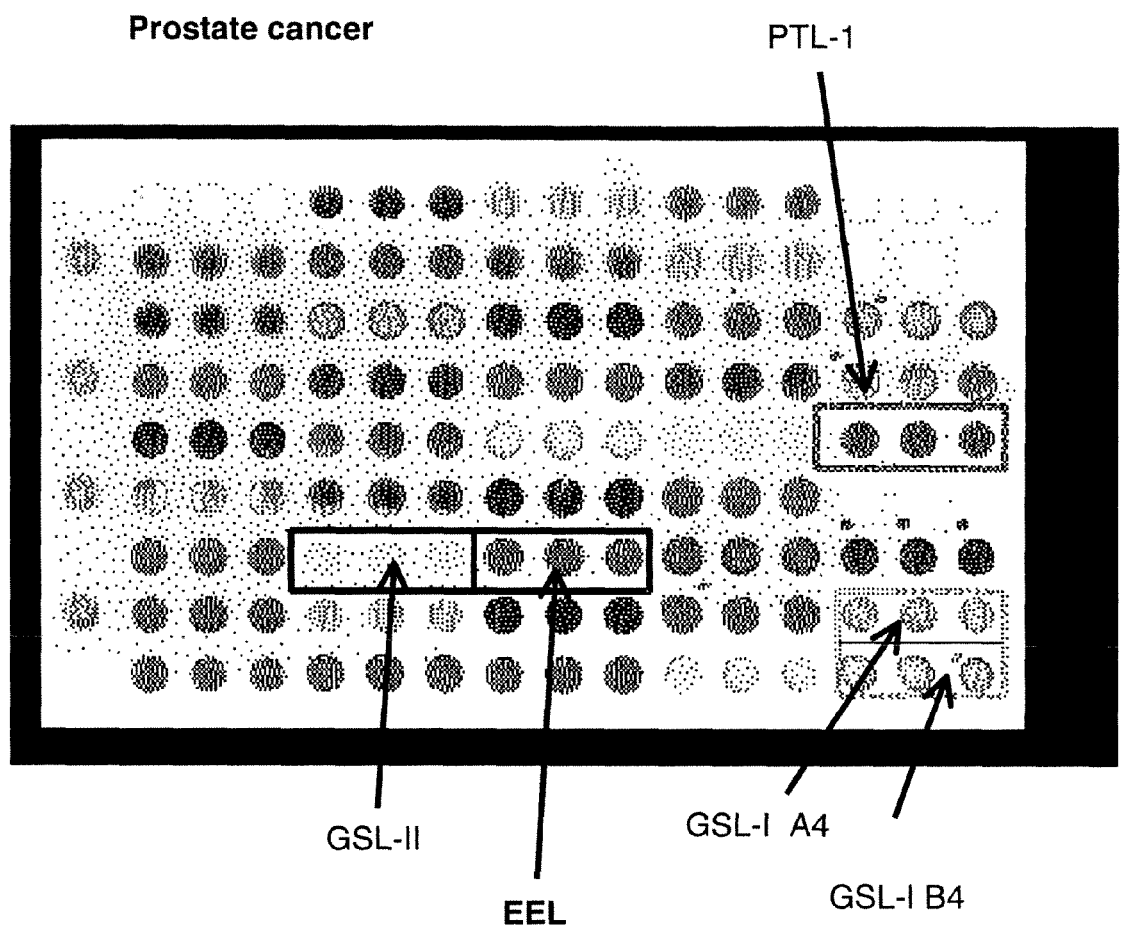
FIG. 8 is a photographic representation of results with the array of FIG. 7 when tested with membrane fractions from prostate cancer cells.
Figure 9:
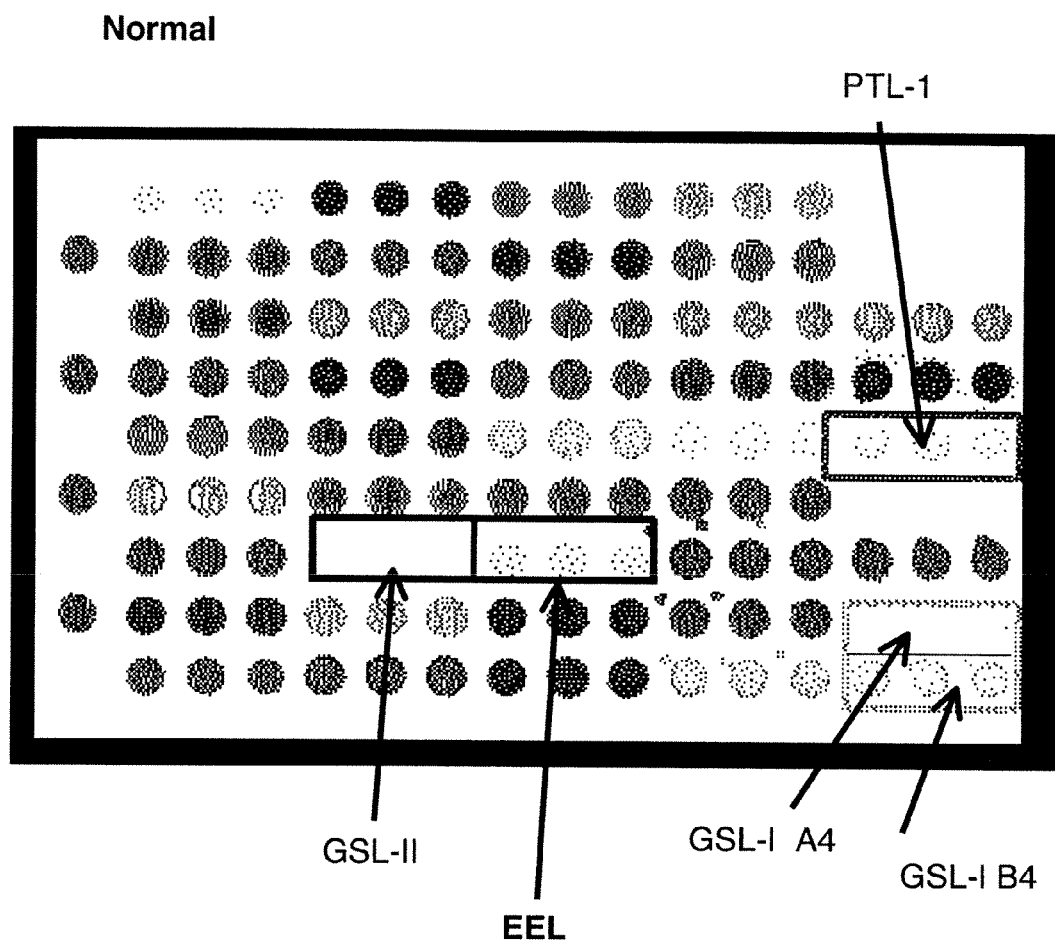
FIG. 9 is a photographic representation of results with the array of FIG. 7 when tested with membrane fractions from normal prostate cells.

Referring now to FIGS. 7-9, these representations of a lectin array illustrate results of different binding to lectins of prostate membrane fractions from different types of prostate cells. The glyco-epitopes exhibited differential amounts of binding to the array, and were visualized by protein-Cy3 conjugates. As is known in the art, Cy3 is an orange fluorescing cyanine dye which can be obtained commercially in a form for linking to compounds containing free amino groups. In the original photographs, different colors (not shown) indicate different degrees of binding. In the present work, 0.1 microgram of a protein-Cy3 conjugate obtained from a membrane fraction of the indicated tissue type was added to each lectin array. The results are from lectin array detection of glyco-epitopes in prostate primary cultures. In FIGS. 8 and 9 are shown array images (FIG. 8, precancerous prostate; FIG. 9, normal prostate). The boxes in the figure indicate that different results, that is, different levels of glyco-epitope expression, were detected by lectin EEL, GSL-1-A4 and GSL-1-B4, and PTL-1, with higher binding in the precancerous cells. FIG. 7 identifies the lectins and their location in the array. The array shown in FIG. 7 is available from Moritex Co. Ltd., Tokyo, Japan. For details on the array itself, see Tateno, et al., "A novel strategy for mammalian cell surface glycome profiling using lectin microarray," *Glycobiology* 2007 17(10): 1138-1146.

Figure 10:
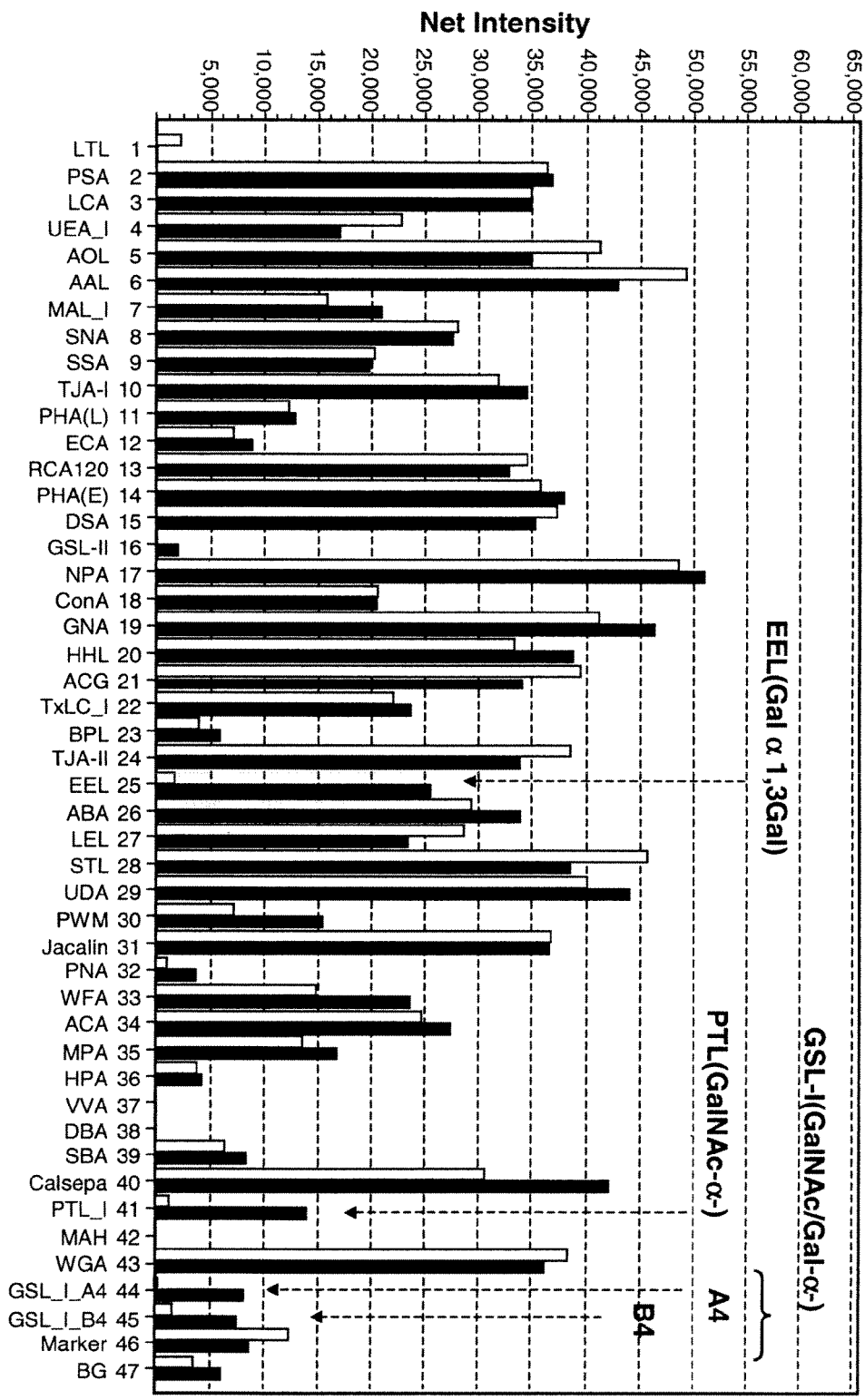
FIG. 10 is a bar graph of the lectin array results illustrated photographically in FIGS. 8 and 9. The white bars are normal tissue and the black bars are from cancerous tissue.
Figure 11:
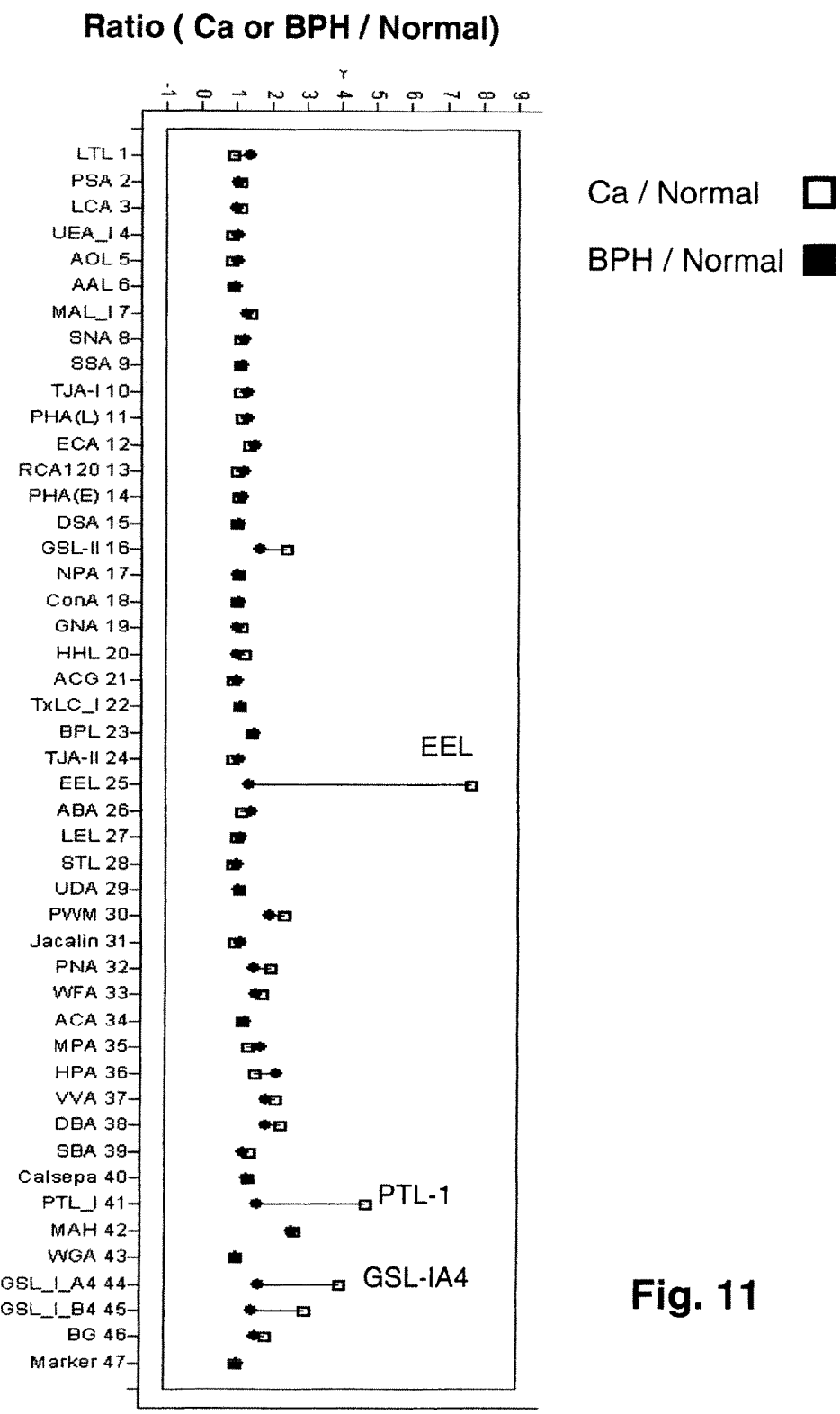
FIG. 11 is line graph illustrating the results of binding of serum antibodies from BPH or prostate cancer patients as a ratio of that binding to antibodies from normal patients. This shows the folds of signal increase in the cancer subject (Ca) or BPH subject as compared to the normal control subject. Probes with significant signal increase in cancer, including EEL, PTL-1, GSL-I A4 and B4, as labeled in the figure with lines.

Referring now to FIG. 10, the bar graph there shows the glyco-epitope profiles of prostate primary cultures. The lectins used are listed from left to right, as follows:

1. LTL
2. PSA
3. LCA
4. UEA-1
5. AOL
6. AAL
7. MAL
8. SNA
9. SSA
10. TJA-1
11. PHAL
12. ECA
13. RCA120
14. PHA-E
15. DSA
16. GSL II
17. NPA
18. ConA
19. GNA
20. HHL
21. ACG
22. TxLC_I
23. BPL
24. TJA II
25. EEL
26. ABA
27 LEL
28. STL
29. UDA
30. PWM
31. Jacalin
32. PNA
33. WFA
34. ACA
35. MPA
36. HPA
37. VVA
38. DBA
39. SBA
40. Calsepa
41. PTL_I
42. MAH
43. WGA
44. GSL_I_A4
45. GSL_I_B4
46. Marker
47. BG Bars 46 and 47 are dye marker and background, respectively. Many of the above lectins are commercially available, e.g., from Vector laboratories or EY Laboratories, whose literature may be consulted for further description of these lectins. In FIG. 10, the white bars are normal tissue and the black bars are from cancerous tissue. Higher binding in cancerous tissue of EEL at position 25, PTL at 41, GSL-1A4 at 44, GSL-a B4 at 45 can be seen. The carbohydrate specificities are given for EEL, PTL-1 and GSL.

Using the Moritex System, glycan structure profiling is performed using a variety of lectins (i.e., glycan binding proteins) with differing glycan binding properties. The lectin microarray is produced by immobilizing 45 lectins with differing glycan specificities onto a slide glass (LecChip™ Ver. 1.0). Cy3-labeled glycoproteins are then applied to the lectin microarray and the resulting fluorescence pattern is scanned by a specially designed glycan profiler (GlycoStation™ Reader1200). The evanescent-field fluorescent excitation technology incorporated in the GlycoStation™ Reader1200 is essential for detecting very weak molecular interactions. Traditional methods require a washing process be applied to the lectin microarray in order to remove redundant proteins which have no binding to lectins. This washing process causes a great deal of affinity information to be lost. Injecting light directly into the lectin microarray slide glass in an internal total reflection mode forms an evanescent-field on the surface of the lower reflective index side. The penetration depth of the evanescent field is a wavelength distance from the surface and the field strength decreases exponentially over the 1 wavelength distance.

Comparing FIGS. 8-10, it can be seen that the EEL (binding to Galα1, 3Gal) bound little to the NM (normal cells) but greatly to the PrCa cells. Significant differentials were also seen with PTL (binding to GalNAc-α), GSL-I (binding to GalNAc/Galα) A4 and B4. PTL-1 is lectin from *Psophocarpus Tetragonolobus*; GSL-1A4 and GSL-1B4 were from *Griffonia Simplicifolia*, A form being GalNac-α and B form being Gal-α.

One can see that many of the lectins bound equally to normal and precancerous prostate cells, but the above-mentioned lectins did not.

Example 3

An Array of Glycans for Detection of Auto-Antibodies

Figure 12:
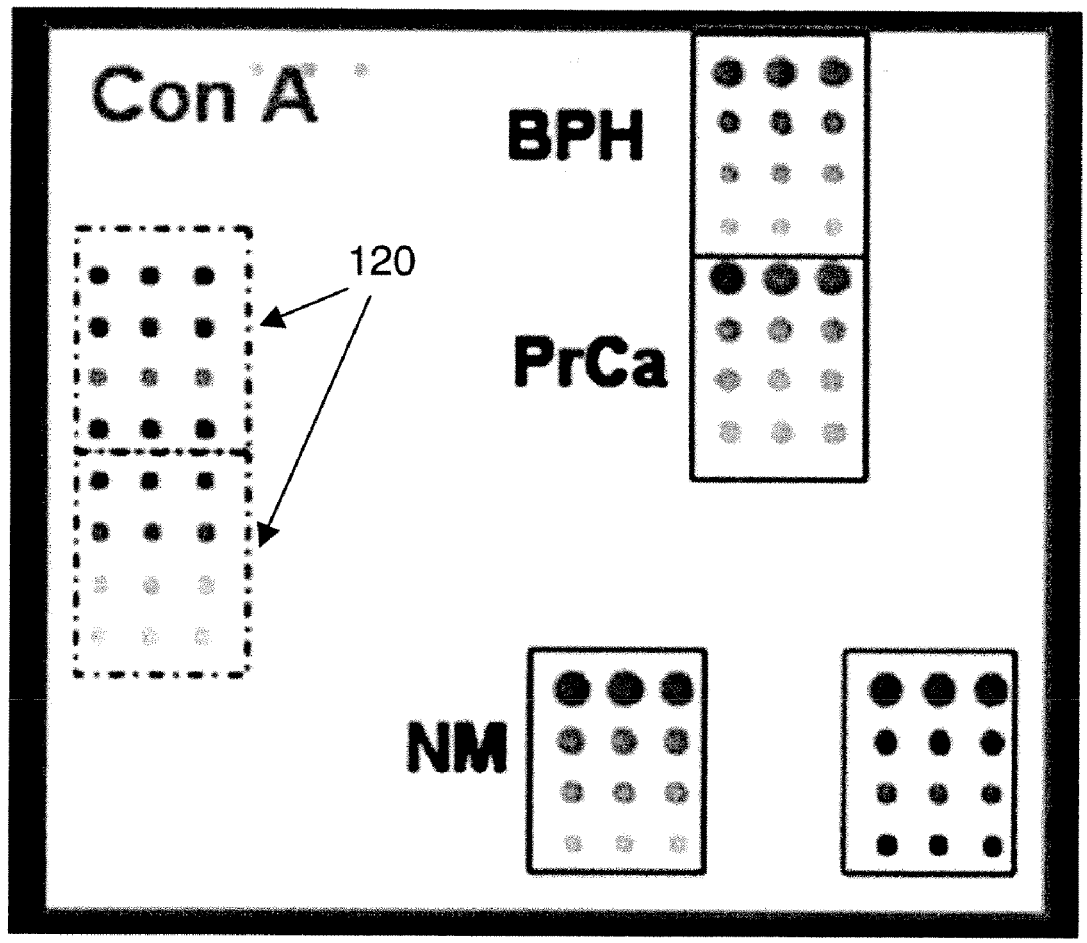
FIG. 12 is an array image showing glycoprotein array validation of the lectin array finding. This figure shows ConA staining of spotted glycoproteins. Locations of cell membrane preparations from normal primary culture (NM), BPH and prostate cancer (PrCa) are marked. ConA positive staining of two Man9-cluster conjugates is marked.
Figure 13:
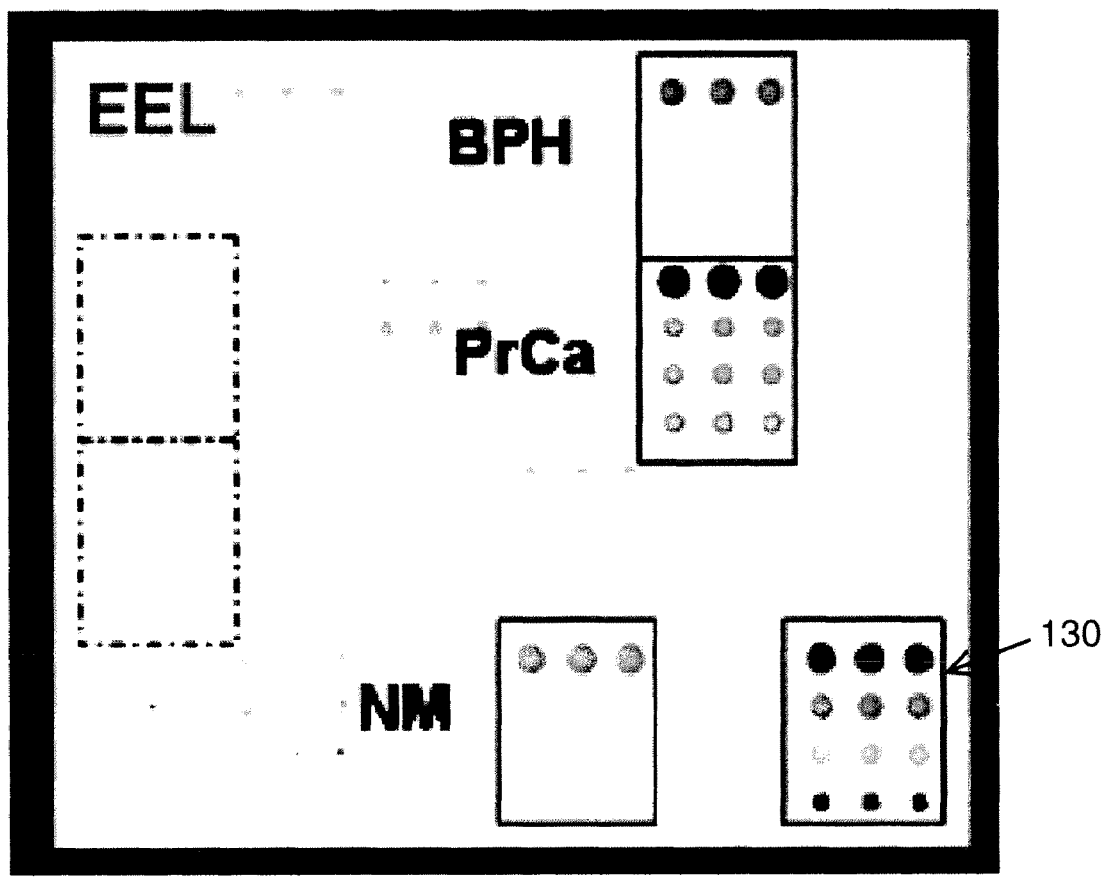
FIG. 13 is an array image as in FIG. 12 but shows EEL staining results.

Images of a glycoprotein array which was tested with various lectins to validate the prostate cancer associated EEL epitope can be seen FIG. 12 and FIG. 13. One can observe that the EEL lectin (FIG. 13) provides different results as between the PrCa (prostate cancer) associated epitopes and the BPH epitopes, whereas the ConA lectin, which recognizes α-linked mannose and terminal glucose residues, does not. It can also be seen that the Man9 is bound specifically by the ConA but not the EEL. Binding of ConA to the Man9 clusters is indicated at 120. In FIG. 13, at 130, it can be seen that the LNCaP are positive in binding to EEL. The LNCaP cell line was established from a metastatic lesion of human prostatic adenocarcinoma. See, Horoszewicz et al., "LNCaP model of human prostatic carcinoma," *Cancer Res*. April 1983; 43(4): 1809-18. Similarly, membrane preparation of PrCa (prostate cancer tissue) shows strong positive.

Carbohydrate Microarrays Identify Autoantibody Reactivities in Prostate Cancers

Recognition of aberrant expression of carbohydrate moieties in prostate cancers has raised important questions as to i) whether their expression is correlated to the malignant transformation and/or progression of prostate cancers; ii) whether these carbohydrate structures are immunogenic in prostate cancer subjects and thereby elicit autoantibodies targeting these structures. The present methods serve to answer these questions. FIG. 3 shows a schematic diagram illustrating how antigenic sugar moieties on cell surfaces can change in the case of abnormal cell conditions (such as cancer). An exemplary class of cryptic sugar moieties of cellular N-glycans is shown. In FIG. 3 the core GlcNAc (N-acetylglucosamine) sugars 302, 304 circles, are linked to a number of mannose residues 306, squares, which in turn are linked to GlcNAc sugars 308, circles, which are in turn linked to a number of galactose sugars 310, triangles, terminating in sialic acid residues 312, indented rectangles. Then, in different modifications, the sialic acid terminii may be removed, or these and the galactose 310 residues may be removed, or the sialic acid 312, galactose 310, outer GalNAc 308 may be removed, leaving only the mannose residues 306. Lectins SNA, PHA-L and GNA are illustrative of lectin-detectible glyco-epitope changes. The native structure containing terminal sialic acid residues may be bound, for example, with the lectin SNA. The structures of FIG. 3 are known to exist in the case of SARS-CoV (a type of coronavirus) modifications, and the GNA/2G12 lectin/antibody binding structures associated with changes due to HIV infection. The Man-core structures are targeted by autoantibodies in the prostate cancer subjects although Tri/m-Gn and Tri/m-II glyco-determinants are also highly expressed in prostate cancer tissues.

On the basis that prostate disease may expose different antigenic determinants, carbohydrate microarrays were used to examine whether autoantibodies to particular carbohydrates are present in serum of prostate cancer subjects. In order to facilitate surface-display and preservation of the "native" antigenic structures of autoantigens, we used the nitrocellulose-based carbohydrate microarray platform. We have demonstrated that this method allows immobilization of polysaccharides, glycoproteins and glycolipids in the same bioarray[44, 45, 48]. Then, we used these bioarrays to characterize the antibody profiles of sera from prostate cancer subjects and the BPH controls. The bioarrays used were composed of 52 distinct antigen preparations, including glycolipids, glycoproteins and polysaccharides. Results from a carbohydrate array are pictured in FIG. 5. The array encompassed diverse cellular N-glycans. For example, members of the N-glycan cryptic structures: Man-cores (FIG. 4) Tri-/m-Gn, and Tri/m-II, were included in these glycan arrays. That is, in addition to preparations of native human glycoprotein OR, ASOR and AGOR depicted in the array in FIG. 5, we applied two synthetic high-mannose-clusters, (Man9)n-KLH and [(Man9)4] n-KLH (FIG. 4). Referring again to FIG. 3, the cryptic glyco-epitopes illustrated there are analogous to the AGOR, having core mannose and GlcNAc; ASOR having an additional layer; and OR, having terminal sialic acid.

Figure 5:
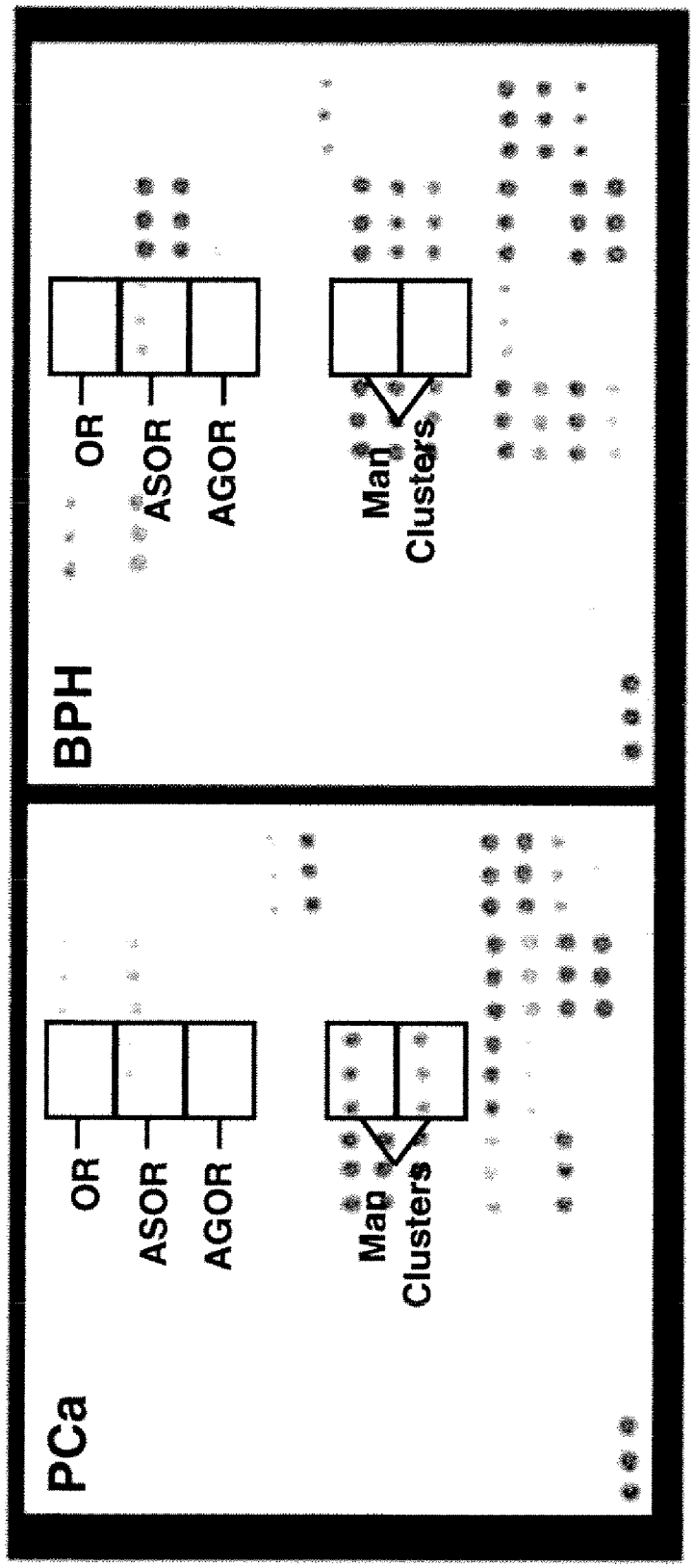
FIG. 5 is a series of array results showing that the Man clusters of FIG. 4, but not OR (orosomucoid) or AGOR (agalacto-orosomucoid) or ASOR (asialo-orosomucoid) give different results in PCa (prostate cancer) and BPH (benign prostate hyperplasis). The two panels shown are a pair of photographs showing the arrays as tested in PCa and BPH.
Figure 6:
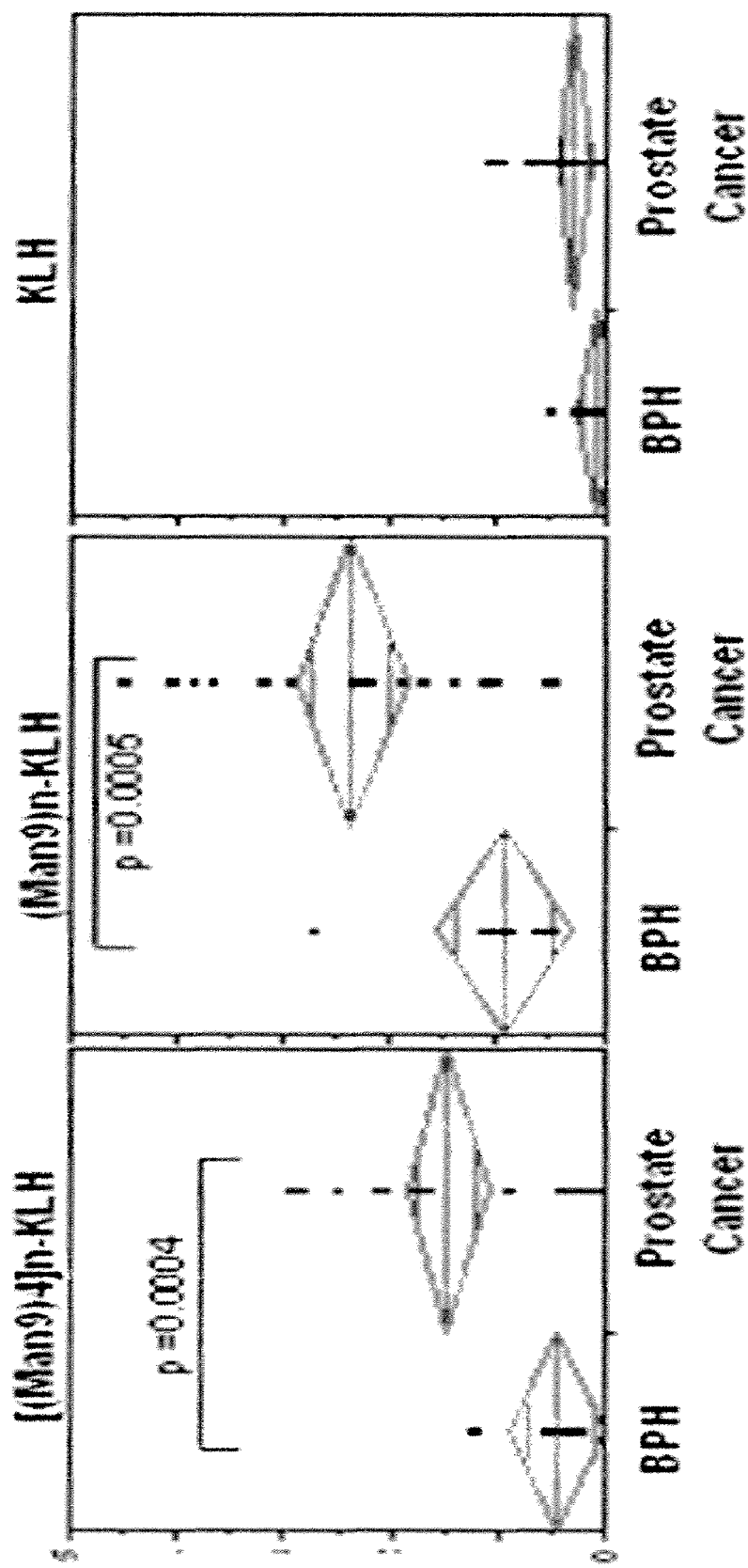
FIG. 6 is a series of three graphs of the results, by array score, showing detection of 2 different glycan probes in the arrays of FIG. 5 when the array was contacted with antibodies from different patients. These are termed "glycan arrays" in that they are used to detect anti-glycan antibodies in bodily fluids. KLH glycoprotein is shown as a control (right panel) but expresses also glycan structures.

FIG. 4 shows structures of the two Man-cluster-KLH conjugates[3-7] that, as glyco-epitopes used in the arrays of FIGS. 5-6, detected significant amounts of IgG antibodies in prostate cancer subjects. These conjugates were designed for HIV vaccines and were kindly provided by Dr. Lai-Xi Wang in the Institute of Human Virology Baltimore, Md.

The two neoglycoconjugates differ in their cluster configurations[3-6]. The former represents high-mannose N-glycans that are generally not detectable in normal cells. The latter mimics the Man-clusters displayed by the gp120 glycoprotein of HIV-1. As a negative control, we spotted also the KLH carrier of these conjugates and yeast phosphomannan on the carbohydrate microarrays.

The structures shown in FIG. 4 represent a (Man9)n-KLH. The structure of Man-9 is known and is illustrated with the indicated circles and squares (mannose and GlcNAc. The maleimide-functionalized Man9 units were applied for conjugation. The carbohydrate contents in these glycoconjugates were about 15%. The preparation of [(Man9)4]n-KLH and (Man9)n-KLH was previously described (*J. Biol. Chem*., Vol. 277, Issue 37, 34336-34342, Sep. 13, 2002. IN)

The carbohydrate array data shown in FIG. 5 is based on sera from seventeen prostate cancer and twelve BPH subjects. In FIG. 6, data for three of these carbohydrate probes are presented, represented by three horizontal lines in each graph. Array datasets were processed and statistically analyzed using SAS Institute's JMP 6.0 software package. Each dot in FIG. 6 is the mean values (IgG score) of triplicate array detection of a subject. The p-values in each panel describe the statistical reliability of the difference in means (between groups) while the means (extended bar) and standard deviations (diamond around the mean value) describe the size of the difference, in relation to the distribution of values in each group. In the upper panel, we show images of carbohydrate microarrays, either stained with serum of a cancer or a BPH subject. Carbohydrate arrays have detected prostate cancer-associated autoantibodies that target Man-clusters. The data in FIG. 6 is also presented below in Table form:

| | Glycan array scores (IgG) | | | | |
| --- | --- | --- | --- | --- | --- |
| | Prostate cancer (n = 17) | | BPH (n = 12) | | t-Test |
| Probes | Mean | SD | Mean | SD | (p values) |
| [(Man$_9$)$_4$]$_n$-KLH | 1.478 | 0.963 | 0.441 | 0.264 | 0.0004 |
| (Man$_9$)$_n$-KLH | 2.367 | 1.304 | 0.927 | 0.597 | 0.0005 |
| SH-KLH | 0.273 | 0.385 | 0.067 | 0.175 | 0.0639 |

Array locations for the different N-glycans (e.g., as illustrated in FIGS. 3 & 4), are marked in FIG. 5. Visual inspection of the images in FIG. 5 reveals marked differences in IgG antibody profiles between the cancer subject and BPH (benign prostate hyperplasia) control, as illustrated by the spot pattern in FIG. 5, comparing the PCa (cancer) with the BPH panel. The prostate cancer subject produced high levels of IgG antibodies against two preparations of high mannose N-glycan clusters [(Man9)4]n-KLH and (Man9)n-KLH which we refer to as "Man-clusters." By contrast, there is no detectable anti-Man cluster IgG antibody in the BPH subject. Given that lectin GNA staining of prostate cancers in tissue arrays is strongly positive (FIG. 2) and that GNA is specific for the Man-core structures, our microarray observation encouraged us to examine an extended panel of serum specimens. The data in FIG. 5 is summarized below in table form:

| Reagent name, preparation code, concentration used for microarray printing | Prostate cancer (n = 17) Mean and SD | | BPH (n = 12) mean and SD | | τ-test (p values) |
|---|---|---|---|---|---|
| AGOR DW38 0.5 mg/ml | 0.179 | 0.303 | 0.225 | 0.209 | 0.63338 |
| AGOR DW38 0.5 mg/ml 1:5 in saline | −0.240 | 0.152 | −0.177 | 0.135 | 0.25008 |
| ASOR DW37 0.5 mg/ml | 0.348 | 0.416 | 0.149 | 0.295 | 0.14306 |
| ASOR DW37 0.5 mg/ml 1:5 in saline | −0.222 | 0.175 | −0.186 | 0.125 | 0.52734 |
| Dextran B1299S DW51 0.5 mg/ml | 3.861 | 4.786 | 4.438 | 6.773 | 0.80249 |
| Dextran B1299S DW51 0.5 mg/ml 1:5 in saline | 0.979 | 1.672 | 1.535 | 2.820 | 0.54899 |
| Dextran B1355S DW50 0.5 mg/ml | 1.701 | 1.501 | 2.996 | 1.925 | 0.06560 |
| Dextran B1355S DW50 0.5 mg/ml 1:5 in saline* | 0.438 | 0.699 | 1.242 | 0.874 | 0.01553 |
| Yeast phosphomannan B2448 DW 41 0.5 mg/ml | 5.183 | 3.864 | 3.820 | 2.606 | 0.26686 |
| Yeast phosphomannan B2448 DW 41 0.5 mg/ml 1:5 in saline | 1.381 | 1.075 | 1.001 | 1.012 | 0.34126 |
| Bacto-Agar DW801 0.5 mg/ml | 6.045 | 3.046 | 6.076 | 4.727 | 0.98460 |
| Cardiolipin/PTC L70905-2 0.4 mg/2 mg/ml | 1.517 | 1.448 | 1.226 | 0.812 | 0.49720 |
| Cardiolipin/PTC L70905-2 0.4 mg/2 mg/ml 1:5 in saline | 0.191 | 0.193 | 0.113 | 0.212 | 0.32013 |
| Cardiolipin/PTC L70905-1 0.1 mg/2 mg/ml | 0.694 | 0.654 | 0.590 | 0.406 | 0.60242 |
| Cardiolipin/PTC L70905-1 0.1 mg/2 mg/ml 1:5 in saline | 0.117 | 0.181 | 0.021 | 0.075 | 0.06218 |
| Ceramide/PTC L70905-9 0.2 mg/ml | −0.093 | 0.156 | −0.096 | 0.096 | 0.93757 |
| Ceramide/PTC L70905-9 0.2 mg/ml 1:5 in saline | −0.227 | 0.098 | −0.192 | 0.110 | 0.38436 |
| Cerebrosides/PTC DW876 L70905-10 0.2 mg/2 mg/ml | −0.019 | 0.343 | −0.101 | 0.087 | 0.35987 |
| Cerebrosides/PTC DW876 L70905-10 0.2 mg/2 mg/ml 1:5 in saline* | −0.268 | 0.103 | −0.182 | 0.101 | 0.03544 |
| D-erythro-Sphingosine/PtC DW867 L70905-5 0.2/2 mg/ml | 0.085 | 0.310 | 0.011 | 0.167 | 0.41267 |
| D-erythro-Sphingosine/PtC DW867 L70905-5 0.2/2 mg/ml 1:5 in saline | −0.150 | 0.130 | −0.166 | 0.115 | 0.73325 |
| DMPS/PtC L70905-11 0.2 mg/2 mg/ml | −0.040 | 0.212 | −0.035 | 0.142 | 0.94828 |
| DMPS/PtC L70905-11 0.2 mg/2 mg/ml 1:5 in saline | −0.232 | 0.079 | −0.181 | 0.108 | 0.17961 |
| E. coli. LPS 5014 DW934 0.5 mg/ml | 0.365 | 2.313 | 0.951 | 1.805 | 0.45090 |
| E. coli. LPS 5014 DW934 0.5 mg/ml 1:5 in saline | −0.246 | 0.317 | 0.048 | 0.478 | 0.07881 |
| E. coli. LPS 2630 DW933 0.5 mg/ml | 0.291 | 0.454 | 0.657 | 0.790 | 0.16729 |
| E. coli. LPS 2630 DW933 0.5 mg/ml 1:5 in saline | −0.094 | 0.278 | 0.142 | 0.379 | 0.08278 |
| E. coli. K1 DW34 0.5 mg/ml | 1.564 | 1.338 | 1.192 | 1.305 | 0.46161 |
| E. coli. K1 DW34 0.5 mg/ml 1:5 in saline | −0.060 | 0.331 | 0.095 | 0.795 | 0.53541 |
| E. coli. K100 DW36 0.5 mg/ml | 3.108 | 2.824 | 4.251 | 3.094 | 0.32087 |
| E. coli. K100 DW36 0.5 mg/ml 1:5 in saline | 0.741 | 1.239 | 1.225 | 1.041 | 0.26494 |
| E. coli. K92 DW92 0.5 mg/ml | 0.204 | 0.518 | 0.023 | 0.281 | 0.23883 |
| E. coli. K92 DW92 0.5 mg/ml 1:5 in saline | −0.280 | 0.156 | −0.211 | 0.111 | 0.17709 |
| Ganglioside/PtC DW866 L70905-4 0.2 mg/2 mg/ml | −0.009 | 0.253 | −0.068 | 0.115 | 0.40170 |
| Ganglioside/PtC DW866 L70905-4 0.2 mg/2 mg/ml 1:5 in Saline | −0.193 | 0.104 | −0.159 | 0.111 | 0.41449 |
| Glucocerebroside/PtC DW871 L70905-7 0.2 mg/2 mg/ml | −0.079 | 0.148 | −0.122 | 0.089 | 0.34495 |
| Glucocerebroside/PtC DW871 L70905-7 0.2 mg/2 mg/ml 1:5 in saline | −0.203 | 0.119 | −0.197 | 0.105 | 0.87167 |
| GM1/PtC L70905-3 0.02 mg/2 mg/ml | 0.087 | 0.285 | 0.036 | 0.207 | 0.58106 |
| GM1/PtC L70905-3 0.02 mg/2 mg/ml 1:5 in saline | −0.130 | 0.086 | −0.092 | 0.127 | 0.38154 |
| KLH-SH DW952 0.5 mg/ml | 0.273 | 0.385 | 0.067 | 0.175 | 0.06388 |
| KLH-SH DW952 0.5 mg/ml 1:5 in saline* | −0.251 | 0.144 | −0.154 | 0.107 | 0.04831 |
| Levan DW42 0.5 mg/ml | 0.892 | 1.607 | 1.703 | 1.374 | 0.15690 |
| Levan DW42 0.5 mg/ml 1:5 in saline* | 0.024 | 0.514 | 0.576 | 0.631 | 0.02092 |
| Man5-9-RB DW949 0.5 mg/ml* | 0.148 | 0.298 | −0.050 | 0.159 | 0.02902 |

-continued

| Reagent name, preparation code, concentration used for microarray printing | Prostate cancer (n = 17) Mean and SD | | BPH (n = 12) mean and SD | | τ-test (p values) |
|---|---|---|---|---|---|
| Man5-9-RB DW949 0.5 mg/ml 1:5 in saline | −0.180 | 0.207 | −0.172 | 0.096 | 0.88286 |
| [(Man9)4]n-KLH DW951 0.5 mg/ml* | 1.478 | 0.963 | 0.441 | 0.264 | 0.00045 |
| [(Man9)4]n-KLH DW951 0.5 mg/ml 1:5 in saline* | 0.174 | 0.462 | −0.127 | 0.119 | 0.01901 |
| (Man9)n-KLH DW950 0.5 mg/ml | 2.367 | 1.304 | 0.927 | 0.597 | 0.00053 |
| (Man9)n-KLH DW950 0.5 mg/ml 1:5 in saline* | 0.561 | 0.701 | 0.047 | 0.290 | 0.01253 |
| Dextran N279 DW49 0.5 mg/ml | 3.976 | 3.419 | 6.866 | 9.622 | 0.33697 |
| Dextran N279 DW49 0.5 mg/ml 1:5 in saline | 2.594 | 2.302 | 4.497 | 6.248 | 0.33160 |
| OR (1) DW749 0.5 mg/ml | −0.281 | 0.158 | −0.184 | 0.142 | 0.09732 |
| OR (1) DW749 0.5 mg/ml 1:5 in saline | −0.303 | 0.147 | −0.234 | 0.123 | 0.17942 |
| Phytosphingosine/PtC DW870 L70905 0.2 mg/2 mg/ml | −0.162 | 0.164 | −0.165 | 0.102 | 0.95493 |
| Phytosphingosine/PtC DW870 L70905 0.2 mg/2 mg/ml 1:5 in saline | −0.218 | 0.107 | −0.242 | 0.146 | 0.63965 |
| PtC L70905012 2 mg/ml | −0.007 | 0.377 | −0.025 | 0.157 | 0.86165 |
| PtC L70905012 2 mg/ml 1:5 in saline | −0.224 | 0.082 | −0.179 | 0.081 | 0.15456 |
| S. dysenterine type I O-SP DW 765 0.5 mg/ml | 2.344 | 2.377 | 2.696 | 3.009 | 0.73871 |
| S. dysenterine type I O-SP DW 765 0.5 mg/ml 1:5 in saline | 1.205 | 2.152 | 1.012 | 1.927 | 0.80189 |
| S. typhi LPS7261 DW932 1:5 in saline | 3.594 | 4.810 | 3.021 | 2.709 | 0.68697 |
| S. typhi LPS7261 DW932 0.5 mg/ml | 6.126 | 6.838 | 5.600 | 5.634 | 0.82255 |
| Sulfatide/PtC L70905-8 0.2 mg/2 mg/ml | 0.067 | 0.285 | −0.065 | 0.109 | 0.09704 |
| Sulfatide/PtC L70905-8 0.2 mg/2 mg/ml 1:5 in saline | −0.193 | 0.174 | −0.199 | 0.111 | 0.91021 |
| Dye mix. (Cy3, Cy5, FITC-AV 1:100) | 16.944 | 8.538 | 14.220 | 8.295 | 0.39797 |

Results with significant difference (t-test, p < 0.05) between prostate cancer group and BPH group are highlighted above in bold with an asterisk.

These carbohydrate array datasets were analyzed using JMP Microarray software from SAS Institute. Antigen-specific IgG reactivity is shown as microarray scores, which are the log 2 transformed (median-background) values normalized by setting their interquartile ranges (IQR) to be identical. We explored several other normalization methods, including mean- and/or variance centering, loess, and quantile normalization, and found IQR to provide an appropriate degree of standardization (based on distribution and correlation plots) without overly correcting the data. After normalization, we utilized an antigen-by-antigen ANOVA model to obtain statistically significant differences. Data from triplicate spots for each antigen were included in the ANOVA model for that antigen.

This statistical analysis has identified markers that show significant differences in IgG antibodies between the two groups: two 'markers' are IgG antibodies that are significantly higher in the prostate cancer group than those in the BPH group and two 'markers' are IgG levels that are lower in the prostate cancer group than those in the BPH group. The former are the two Man-clusters; the latter include microbial polysaccharides, dextran B1355s and levan. Data for the two Man-clusters and a control reagent (a KLH carrier) are illustrated in FIG. 6.

Given that we did not detect significant difference in antibody activity with the yeast phosphomannan and the KLH carrier spotted in the same arrays, the anti-Man antibody specificities are thought to be directed at the high mannose-type N-glycans that occur on mammalian cells, but not those on the microbial polysaccharide phosphomannan. This work has identified anti-Man-clusters IgG antibodies as potential serum biomarkers of prostate cancers for further investigation.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

REFERENCES

1. Stamey, T. A. et al. Localized prostate cancer. Relationship of tumor volume to clinical significance for treatment of prostate cancer. *Cancer* 71, 933-938 (1993).
2. Ries, L. A. Influence of extent of disease, histology, and demographic factors on lung cancer survival in the SEER population-based data. *Semin Surg Oncol* 10, 21-30 (1994).
3. Wang, L. X., Ni, J., Singh, S. & Li, H. Binding of high-mannose-type oligosaccharides and synthetic oligomannose clusters to human antibody 2G12: implications for HIV-1 vaccine design. *Chem Biol* 11, 127-134 (2004).
4. Wang, L. X. Toward oligosaccharide- and glycopeptide-based HIV vaccines. *Curr Opin Drug Discov Devel* 9, 194-206 (2006).
5. Ni, J., Song, H., Wang, Y., Stamatos, N. M. & Wang, L. X. Toward a carbohydrate-based HIV-1 vaccine: synthesis and immunological studies of oligomannose-containing glycoconjugates. *Bioconjug Chem* 17, 493-500 (2006).
6. Li, H. & Wang, L. X. Design and synthesis of a template-assembled oligomannose cluster as an epitope mimic for human HIV-neutralizing antibody 2G12. *Org Biomol Chem* 2, 483-488 (2004).
7. Wang, D. From a single antigen to a carbohydrate microarray: Dr. Kabat's recurring influence. *Elvin A. Kabat Memorial Symposium* (Speaker) (2001).
8. Stamey, T. A. et al. Prostate-specific antigen as a serum marker for adenocarcinoma of the prostate. *N Engl J Med* 317, 909-916 (1987).
9. Presti, J. C., Jr., O'Dowd, G. J., Miller, M. C., Mattu, R. & Veltri, R. W. Extended peripheral zone biopsy schemes increase cancer detection rates and minimize variance in prostate specific antigen and age related cancer rates: results of a community multi-practice study. *J Urol* 169, 125-129 (2003).
10. Stewart, C. S., Leibovich, B. C., Weaver, A. L. & Lieber, M. M. Prostate cancer diagnosis using a saturation needle biopsy technique after previous negative sextant biopsies. *J Urol* 166, 86-91; discussion 91-82 (2001).
11. Stamey, T. A. et al. The prostate specific antigen era in the United States is over for prostate cancer: what happened in the last 20 years? *J Urol* 172, 1297-1301 (2004).
12. Stamey, T. A., McNeal, J. E., Yemoto, C. M., Sigal, B. M. & Johnstone, I. M. Biological determinants of cancer progression in men with prostate cancer. *Jama* 281, 1395-1400 (1999).
13. Noguchi, M., Stamey, T. A., McNeal, J. E. & Yemoto, C. M. Relationship between systematic biopsies and histological features of 222 radical prostatectomy specimens: lack of prediction of tumor significance for men with nonpalpable prostate cancer. *J Urol* 166, 104-109; discussion 109-110 (2001).
14. King, C. R., McNeal, J. E., Gill, H. & Presti, J. C., Jr. Extended prostate biopsy scheme improves reliability of Gleason grading: implications for radiotherapy patients. *Int J Radiat Oncol Biol Phys* 59, 386-391 (2004).
15. De Marzo, A. M. et al. Pathological and molecular mechanisms of prostate carcinogenesis: implications for diagnosis, detection, prevention, and treatment. *J Cell Biochem* 91, 459-477 (2004).
16. Adam, B. L. et al. Serum protein fingerprinting coupled with a pattern-matching algorithm distinguishes prostate cancer from benign prostate hyperplasia and healthy men. *Cancer Res* 62, 3609-3614 (2002).
17. Li, J. et al. Detection of prostate cancer using serum proteomics pattern in a histologically confirmed population. *J Urol* 171, 1782-1787 (2004).
18. Diamandis, E. P. Analysis of serum proteomic patterns for early cancer diagnosis: drawing attention to potential problems. *J Natl Cancer Inst* 96, 353-356 (2004).
19. George, D. J. et al. Radical prostatectomy lowers plasma vascular endothelial growth factor levels in patients with prostate cancer. *Urology* 63, 327-332 (2004).
20. Wang, X. et al. Autoantibody signatures in prostate cancer. *N Engl J Med* 353, 1224-1235 (2005).
21. Prakash, S. & Robbins, P. W. Glycotyping of prostate specific antigen. *Glycobiology* 10, 173-176 (2000).
22. Peracaula, R. et al. Altered glycosylation pattern allows the distinction between prostate-specific antigen (PSA) from normal and tumor origins. *Glycobiology* 13, 457-470 (2003).
23. Ohyama, C. et al. Carbohydrate structure and differential binding of prostate specific antigen to *Maackia amurensis* lectin between prostate cancer and benign prostate hypertrophy. *Glycobiology* 14, 671-679 (2004).
24. Keding, S. J. & Danishefsky, S. J. Prospects for total synthesis: a vision for a totally synthetic vaccine targeting epithelial tumors. *Proc Natl Acad Sci USA* 101, 11937-11942 (2004).
25. Li, R., Yao, J. L., Bourne, P. A., di Sant'Agnese, P. A. & Huang, J. Frequent expression of human carcinoma-associated antigen, a mucin-type glycoprotein, in cells of prostatic carcinoma. *Arch Pathol Lab Med* 128, 1412-1417 (2004).
26. Fukuda, M. Possible roles of tumor-associated carbohydrate antigens. *Cancer Res* 56, 2237-2244 (1996).
27. Hakomori, S. Glycosylation defining cancer malignancy: new wine in an old bottle. *Proc Natl Acad Sci USA* 99, 10231-10233 (2002).
28. Feizi, T. Demonstration by monoclonal antibodies that carbohydrate structures of glycoproteins and glycolipids are onco-developmental antigens. *Nature* 314, 53-57 (1985).
29. Hakomori, S. Aberrant glycosylation in cancer cell membranes as focused on glycolipids: overview and perspectives. *Cancer Res* 45, 2405-2414 (1985).
30. Moriyama, H., Nakano, H., Igawa, M. & Nihira, H. T antigen expression in benign hyperplasia and adenocarcinoma of the prostate. *Urol Int* 42, 120-123 (1987).
31. Ghazizadeh, M., Kagawa, S., Izumi, K. & Kurokawa, K. Immunohistochemical localization of T antigen-like substance in benign hyperplasia and adenocarcinoma of the prostate. *J Urol* 132, 1127-1130 (1984).
32. Zhang, S. et al. Expression of potential target antigens for immunotherapy on primary and metastatic prostate cancers. *Clin Cancer Res* 4, 295-302 (1998).
33. Slovin, S. F. et al. Thomsen-Friedenreich (TF) antigen as a target for prostate cancer vaccine: clinical trial results with TF cluster (c)-KLH plus QS21 conjugate vaccine in patients with biochemically relapsed prostate cancer. *Cancer Immunol Immunother* 54, 694-702 (2005).
34. Slovin, S. F. et al. A bivalent conjugate vaccine in the treatment of biochemically relapsed prostate cancer: a study of glycosylated MUC-2-KLH and Globo H-KLH conjugate vaccines given with the new semi-synthetic saponin immunological adjuvant GPI-0100 OR QS-21. *Vaccine* 23, 3114-3122 (2005).
35. Morse, M. A. Technology evaluation: Theratope, Biomira Inc. *Curr Opin Mol Ther* 2, 453-458 (2000).
36. Abel, P. D. et al. Detection of blood group antigens in frozen sections of prostatic epithelium. *Br J Urol* 59, 430-435 (1987).
37. Satoh, M. et al. Glycolipid expression in prostatic tissue and analysis of the antigen recognized by antiprostatic monoclonal antibody APG1. *Urol Int* 48, 20-24 (1992).
38. Martensson, S. et al. Sialyl-Lewis(x) and related carbohydrate antigens in the prostate. *Hum Pathol* 26, 735-739 (1995).
39. Chandrasekaran, E. V. et al. Analysis of the specificity of sialyltransferases toward mucin core 2, globo, and related structures. identification of the sialylation sequence and the effects of sulfate, fucose, methyl, and fluoro substituents of the carbohydrate chain in the biosynthesis of selectin and siglec ligands, and novel sialylation by cloned alpha2,3(O)sialyltransferase. *Biochemistry* 44, 15619-15635 (2005).
40. Abel, P. D., Cornell, C., Buamah, P. K. & Williams, G. Assessment of serum CA 19.9 as a tumour marker in patients with carcinoma of the bladder and prostate. *Br J Urol* 59, 427-429 (1987).

41. Jorgensen, T. et al. Up-regulation of the oligosaccharide sialyl LewisX: a new prognostic parameter in metastatic prostate cancer. *Cancer Res* 55, 1817-1819 (1995).
42. Ekins, R., Chu, F. & Biggart, E. Multispot, multianalyte, immunoassay. *Ann Biol Clin* 48, 655-666 (1990).
43. Stoll, D. et al. Protein microarray technology. *Front Biosci* 7, C13-32. (2002).
44. Wang, D. & Lu, J. Glycan arrays lead to the discovery of autoimmunogenic activity of SARS-CoV. *Physiol Genomics* 18, 245-248 (2004).
45. Wang, D., Liu, S., Trummer, B. J., Deng, C. & Wang, A. Carbohydrate microarrays for the recognition of cross-reactive molecular markers of microbes and host cells. *Nat Biotechnol* 20, 275-281. (2002).
46. Wang, D. Carbohydrate microarrays. *Proteomics* 3, 2167-2175 (2003).
47. Carroll, G. T., Wang, D., Turro, N. J. & Koberstein, J. T. Photochemical micropatterning of carbohydrates on a surface. *Langmuir* 22, 2899-2905 (2006).
48. Fukui, S., Feizi, T., Galustian, C., Lawson, A. M. & Chai, W. Oligosaccharide microarrays for high-throughput detection and specificity assignments of carbohydrate-protein interactions. *Nat Biotechnol* 20, 1011-1017 (2002).
49. Palma, A. S. et al. Ligands for the beta-glucan receptor, Dectin-1, assigned using "designer" microarrays of oligosaccharide probes (neoglycolipids) generated from glucan polysaccharides. *J Biol Chem* 281, 5771-5779 (2006).
50. Schwartz, A. L., Fridovich, S. E., Knowles, B. B. & Lodish, H. F. Characterization of the asialoglycoprotein receptor in a continuous hepatoma line. *J Biol Chem* 256, 8878-8881 (1981).
51. Wall, D. A., Wilson, G. & Hubbard, A. L. The galactose-specific recognition system of mammalian liver: the route of ligand internalization in rat hepatocytes. *Cell* 21, 79-93 (1980).
52. Feizi, T., Kabat, E. A., Vicari, G., Anderson, B. & Marsh, W. L. Immunochemical studies on blood groups. XLVII. The I antigen complex—precursors in the A, B, H, Lea, and leb blood group system—hemagglutination-inhibition studies. *J Exp Med* 133, 39-52 (1971).
53. Mage, R. G. & Feizi, T. in Nat' Academies Press, Vol. 85 98-123 (National Academy of Sciences, 2004).
54. Janczuk, A. J., Zhang, W., Andreana, P. R., Warrick, J. & Wang, P. G. The synthesis of deoxy-alpha-Gal epitope derivatives for the evaluation of an anti-alpha-Gal antibody binding. *Carbohydr Res* 337, 1247-1259 (2002).
55. Chen, H. T. & Kabat, E. A. Immunochemical studies on blood groups. The combining site specificities of mouse monoclonal hybridoma anti-A and anti-B. *J Biol Chem* 260, 13208-13217 (1985).
56. Wang, D., Wells, S. M., Stall, A. M. & Kabat, E. A. Reaction of germinal centers in the T-cell-independent response to the bacterial polysaccharide alpha(1→6)dextran. *Proc Natl Acad Sci USA* 91, 2502-2506 (1994).

What is claimed is:

1. A method for testing for prostate dysplasia in a subject, comprising the steps of:
    (a) obtaining an antibody-containing sample from the subject; and
    (b) determining the level of antibody in the sample binding specifically to a mannose core structure wherein the said mannose core structure being a high mannose cluster of (man9)n or [(man9)4]n;
    (c) wherein a higher level of antibody compared to that of a control sample is indicative of said prostate dysplasia.
2. The method of claim 1 where the sample is serum.
3. The method of claim 1 where the mannose core structure is attached to a carrier protein.
4. The method of claim 1 further comprising the step of contacting the sample with OR (orosomucoid) or AGOR (agalacto-orosomucoid) or ASOR (asialo-orosomucoid) as a negative control where antibodies from a patient with prostate cancer do not bind to these antigens but do bind to the mannose core structure.
5. The method of claim 1 where the mannose core structure is immobilized in a microarray.
6. The method of claim 1 where the microarray includes both (man9)n and [(man9)4]n.

\* \* \* \* \*

UNITED STATES PATENT AND TRADEMARK OFFICE
CERTIFICATE OF CORRECTION

PATENT NO.        : 7,981,625 B2
APPLICATION NO.   : 12/421964
DATED             : July 19, 2011
INVENTOR(S)       : Denong Wang et al.

It is certified that error appears in the above-identified patent and that said Letters Patent is hereby corrected as shown below:

Title Page, Item (57) in the abstract, line 7, "bound" should be changed to --bind--; line 10, insert the word --are-- after the second occurrence of the word "that"; line 15, the formula reading "(SNA-I" should read --(SNA-I)-- and the formula reading "(PHA-L" should read --(PHA-L)--.
Column 2, line 67, the numbers "26-29" should read --$^{26, 29}$--.
Column 3, line 7, cancel the text "H Lewisa (Lea) and Leb" and replace with --H, Lewisa (Le$^a$) and Le$^b$--; line 8, cancel the text "Lex, Ley, sialyl-Lex and sialyl-Lea" and replace with --Le$^x$, Le$^y$, sialyl-Le$^x$ and sialyl-Le$^a$--; line 22, cancel the text "Ley" and replace with --Le$^y$--; line 23, cancel the text "sialyl-Lex" and replace with --sialyl-Le$^x$--; line 24, cancel the text "Leb$^{39}$" and replace with --Le$^{b39}$--; line 25, cancel the text "Lea$^{40}$" and replace with --Le$^{a40}$--; line 26, cancel the text "sialyl-Lex" and replace with --sialyl-Le$^x$--.
Column 7, line 35, insert --.-- after the word "too".
Column 8, line 63, cancel the text "42, 43" and replace with --$^{42,43}$--.
Column 14, line 58, after "samples" insert --,--.
Column 16, line 31, cancel the text "laboratories" and replace with --Laboratories--.
Column 17, line 12, after "seen" insert --in--; line 40 after "304" insert --,--.
Column 18, line 22, after "Virology" insert --,--; line 32, after "GlcNAc." insert --)--.

Signed and Sealed this
Twenty-ninth Day of May, 2012

David J. Kappos
*Director of the United States Patent and Trademark Office*